(12) United States Patent
Fischer

(10) Patent No.: US 7,279,162 B1
(45) Date of Patent: Oct. 9, 2007

(54) ISOLATED BROADLY REACTIVE OPSONIC IMMUNOGLOBULIN FOR TREATING A PATHOGENIC COAGULASE-NEGATIVE STAPHYLOCOCCUS INFECTION

(75) Inventor: Gerald W. Fischer, Bethesda, MD (US)

(73) Assignee: Henry M. Jackson Foundation for the Advancement of Military Medicine, Rockville, MD (US)

(*) Notice: Subject to any disclaimer, the term of this patent is extended or adjusted under 35 U.S.C. 154(b) by 0 days.

(21) Appl. No.: 08/471,285

(22) Filed: Jun. 6, 1995

Related U.S. Application Data

(60) Division of application No. 08/308,495, filed on Sep. 21, 1994, now abandoned, which is a continuation-in-part of application No. 08/033,476, filed on Mar. 18, 1993, now abandoned, which is a continuation-in-part of application No. 07/854,027, filed on Mar. 19, 1992, now abandoned, which is a continuation-in-part of application No. 07/804,317, filed on Feb. 25, 1992, now abandoned, which is a continuation of application No. 07/601,089, filed on Oct. 22, 1990, now abandoned.

(51) Int. Cl.
*A61K 39/40* (2006.01)
(52) U.S. Cl. ............... 424/165.1; 424/130.1; 424/164.1; 530/350; 530/387.1; 435/7.33
(58) Field of Classification Search ............ 435/7.32, 435/101; 530/395; 424/92, 85.5; 514/54
See application file for complete search history.

(56) References Cited

U.S. PATENT DOCUMENTS

| | | | | |
|---|---|---|---|---|
| 4,027,010 A | * | 5/1977 | Kiselev et al. ............ | 424/87 |
| 4,197,290 A | * | 4/1980 | Yoshida .................... | 424/92 |
| 4,425,330 A | | 1/1984 | Norcross et al. .......... | 424/92 |
| 4,460,575 A | * | 7/1984 | d'Hinterland et al. ..... | 424/92 |
| 4,482,483 A | | 11/1984 | Curry et al. ............... | 260/112 |
| 4,719,290 A | | 1/1988 | Curry et al. ............... | 530/387 |
| 4,732,757 A | | 3/1988 | Stolle et al. ................ | 424/87 |
| 4,789,735 A | * | 12/1988 | Frank et al. ............... | 530/395 |
| 4,830,852 A | * | 5/1989 | Marburg et al. ........... | 424/85.5 |
| 4,902,616 A | * | 2/1990 | Fournier et al. ........... | 435/101 |

(Continued)

FOREIGN PATENT DOCUMENTS

FR 0724016 A 7/1996 .............. 15/12

(Continued)

OTHER PUBLICATIONS

Plaunt et al, J Clin. Microbiology, May 1991, pp. 857-861, vol. 29(5).*

(Continued)

*Primary Examiner*—Dave Trong Nguyen
*Assistant Examiner*—Ginny Allen Portner
(74) *Attorney, Agent, or Firm*—Lahive & Cockfield LLP; Amy E. Mandragouras, Esq.; Megan E. Williams

(57) ABSTRACT

The invention describes the identification, making, and isolation of immunoglobulin and antigen useful for preventing, diagnosing, and treating staphylococcal infections. The invention further describes an in vivo animal model useful for testing the efficacy of pharmaceutical compositions, including pharmaceutical compositions of immunoglobulin and isolated antigen.

12 Claims, 13 Drawing Sheets

Figure 1:
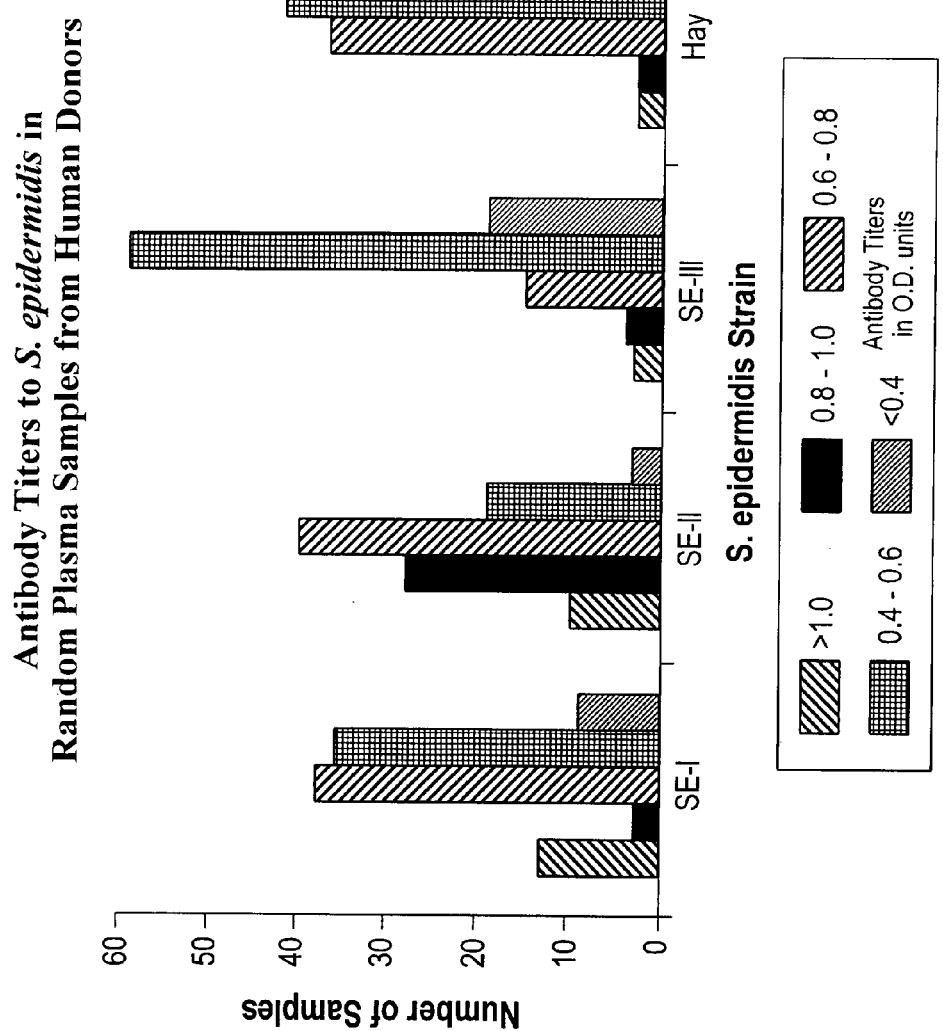

Pre- and Post-Immunization Titers
Whole-cell Vaccine

U.S. PATENT DOCUMENTS

| | | | | |
|---|---|---|---|---|
| 5,034,515 | A | | 7/1991 | Proctor ........................ 536/1.1 |
| 5,055,455 | A | * | 10/1991 | Pier ............................ 514/54 |
| 5,153,312 | A | | 10/1992 | Porro |
| 5,175,096 | A | | 12/1992 | Höök et al. .................. 435/69.1 |
| 5,354,654 | A | | 10/1994 | Ligler et al. ..................... 435/5 |
| 5,440,014 | A | | 8/1995 | Höök et al. .................. 530/326 |
| 5,505,945 | A | | 4/1996 | Gristina et al. .......... 424/164.1 |
| 5,530,102 | A | | 6/1996 | Gristina et al. .......... 530/391.1 |
| 5,538,733 | A | | 7/1996 | Emery et al. ............... 424/422 |
| 5,545,721 | A | | 8/1996 | Carroll et al. ........... 530/391.7 |
| 5,571,511 | A | | 11/1996 | Fischer .................... 424/165.1 |
| 5,624,904 | A | | 4/1997 | Krieger et al. ................ 514/21 |
| 5,652,217 | A | | 7/1997 | Höök et al. .................... 514/12 |
| 5,770,208 | A | | 6/1998 | Fattom et al. .......... 424/197.11 |
| 5,840,846 | A | | 11/1998 | Höök et al. ................. 530/350 |
| 5,851,535 | A | | 12/1998 | Jolivet-Reynaud ....... 424/273.1 |
| 5,955,074 | A | | 9/1999 | Fischer .................... 424/130.1 |
| 5,955,078 | A | | 9/1999 | Burnham et al. ........ 424/190.1 |

FOREIGN PATENT DOCUMENTS

| | | | |
|---|---|---|---|
| WO | 90/03398 | * | 4/1990 |
| WO | 93/09811 | * | 5/1993 |
| WO | WO93/09811 | | 5/1993 |
| WO | WO93/19373 | | 9/1993 |

OTHER PUBLICATIONS

Etzioni , A et al, ACTA Padiatr Scand 79, pp. 156-161, 1990.*
Fattom, A et al, Infect. & Immnun., Jul. 1990, pp. 2367-2374, vol. 58(7).*
Smith , D. G. E.et al, Infect. & Immun., Feb. 1991, pp. 617-624, vol. 59(2).*
Van Bronswijk et al, Immunology, 1989, vol. 67, pp. 81-86.*
Boslego, J.W. et al, Pergamon Press 1991, p. 211-223, In:Vaccine & Immuno-Therapy.*
Ichiman et al, J. Applied Bacteriology, 1987, vol. 63,pp. 165-169.*
Yoshida, K et al, Journal of Canadian Microbiology, vol. 34, 1988, pp. 913-915.*
Yang et al, The Journal of Infectious Diseases, vol. 159(4) Apr. 1989.*
Yoshida, K et al, Journal of Applied Bacteriology, 1988, vol. 65, pp. 491-499.*
BIO, Oct. 17, 1994, Critical Synergy: The Biotechnology Industry and Intellectual Property Protection, p. 101.*
Journal of Medical Microbiology, vol. 35, pp. 65-71, Oxford, U K.*
Timmerman et al. Infect. & Immunity, Nov. 1991, vol. 59(11), pp. 4187-4192.*
Modun ,B et al, Infection and Immunity, Sep. 1994, pp. 3850-3858, vol. 62(9).*
Modun, B et al, Infection and Immunity, Jun. 1992, pp. 2551-2553, vol. 60(6).*
Wilcox, M.H. et al, Journal of General Microbiology, 1991, pp. 2561-2570.*
Timmerman et al, J. Med. Microbiol., vol. 35, 1991, pp. 65-71.*
Fischer, 1988, Ped. Clinics of North Am. 35:517-533.*
Ichiman et al, Journal of Applied Bacteriology, vol. 63, pp. 165-169, 1987.*
Yoshida et al, Canadian Journal of Microbiology, vol. 34,pp. 913-915, 1988.*
van Bronswijk et al, Immunology, 1989, vol. 67, pp. 81-86, 1989.*
Baker et al, May, Pediatric Research, vol. 25(6 part 2), p. 275A, 1989.*
Fischer, Pediatric Clinics of North America, vol. 35(3), Jun. pp. 517-533, 1988.*
Wedren, Scand. J. Urol., Suppl, vol. 123, pp. 1-36, 1989.*
Verhoef, J et al, Scand. J. Infect. Dis., Suppl. 41, pp. 56-63, 1983.*
Fleer et al, Pediatric Infectious Disease, vol. 2(6), pp. 426-431, 1983.*
Thorig et al, Infection, vol. 8(6), pp. 267-274, 1980.*
Clark et al, Journal of Clinical Pathology, vol. 39, pp. 856-860, 1986.*
Espersen, et al, ACTA Pathology Microbiol. Scand., Aug. 1981, vol. 89(4), pp. 253-260.*
Clark et al, J. Clin Path. , vol. 39, pp. 856-860, 1986.*
Fischer, G.W., New Topics in Pediatric Infectious Disease, vol. 35(3), Jun. 1988.*
Ichiman, Y et al, J. Applied Bacteriology, vol. 63, pp. 165-169, 1987.*
Baker, C,.J. et al, Pediatric Res. vol. 25(6 part 2), p. 275A (abstact), 1989.*
Haque, K N, et al, AJDC, vol. 142, Dec., pp. 1293-1296, 1988.*
Yamada, T et al, J. Clin. Microbiology, Oct. 1988, vol. 26(10), pp. 2167-2172.*
Kojima, Y et al, J. Infectious Disease, vol. 162, pates 435-441, 1990.*
Lamperi, S. et al, Biomat. Art. Cells, Art. Org., vol. 15(1), pp. 151-159, 1987.*
Fleer, A et al, J. Infectious Disease, vol. 152(5), Nov. , pp. 930-937, 1985.*
Ahmed, A et al, J. Applied Bacteriology, vol. 69, pp. 676-685, 1990.*
Yang, K.D. et al, J. Infectious Diseases, vol. 159(4), pp. 701-707, Apr. 1989.*
Espersen, F et al, J. Clinical Microbiology, Feb. 1986, vol. 23(2), pp. 339-342.*
Espersen, F et al, ACTA Pathol. Microbiol. Scand. (Denmark), Aug. 1981, vol. 89(4), pp. 253-260.*
Yoshida, K et al, Can. J. Microbiology, vol. 34, pp. 913-915, 1988.*
Etzioni, A et al, ACTA Paediatr. Scand. vol. 79, p. 156-161, 1986.*
Ichiman et al., "Relation of Human Serum Antibody Against *Staphylococcus epidermidis* Cell Surface Polysaccharide Detected by Enzyme-linked Immunosorbent Assay to Passive Protection in the Mouse," *J. Appl. Bacteriol.*, 71:176-181 (1991).
Ichiman et al., "Monoclonal IgM Antibody Protection in Mice Against Infection with an Encapsulated Strain of *Staphylococcus epidermidis,*" *Can. J. Microbiol.*, 37:404-407 (1991).
Fischer et al., "Directed Immune Globulin Enhances Survival in an Intralipid Induced Neonatal Model of Lethal *Staphylococcus epidermidis* Sepsis," *Pediatr. Res.*, Abstract No. 1670, p. 281A (Apr. 1991).
C.C. Patrick, "Coagulase-negative Staphylococci: Pathogens with Increasing Clinical Significance," *J. of Pediatr.*, 116:497-507 (1990).
Freeman et al., "Association of Intravenous Lipid Emulsion and Coagulase-negative Staphylococcal Bacteremia in Neonatal Intensive Care Units," *New. Engl. J. Med.*, 323:301-308 (1990).
J. O. Klein, "From Harmless Commensal to Invasive Pathogen: Coagulase-Negative Staphylococci," *New Engl. J. Med.*, 323:339-340 (1990).
T. Niizuma, "Passive Protective Activities of Specific Human Immuno-globulin Against Strain ST67P of *Staphylococcus hyicus* Extracted from Pooled Human Sera," *Chem. Abstracts*, 115:181022v, p. 713 (1990).
T. Niizuma, "Passive Protection Activities of Specific Human Immunoglobulin Against Strain ST67P of *Staphylococcus hyicus* Extracted from Pooled Human Sera," *St. Marianna Med. J.*, 18:940-946 (1990).
Certified English translation of document No. 10.
Espersen et al., "Solid Phase Radioimmunoassay for IgG Antibodies to *Staphylococcus epidermis*: Use in Serious Coagulase-negative Staphylococcal Infections," *Arch. Intern. Med.*, 147:689-693 (1987).
Ichiman et al., "Protective Antobodies in Human Sera Against Encapsulated Strains of *Staphylococcus epidermidis,*" *J. Appl. Bacteriol.*, 63:165-169 (1987).
Clark et. Al., "Opsonic Activity of Intravenous Immunoglobulin Preparations Against *Staphylococcus epidermidis,*" *J. Clin. Pathol.*, 39:856-860 (1986).
Clark et al., "Opsonic Requirements of *Staphylococcus epidermidis,*" *J. Med. Microbiol.*, 22:1-7 (1986).
Fleer et al., "Opsonic Defense to *Staphylococcus epidermidis* in the Premature Neonate," *J. Infect. Dis.*, 152:930-937 (1985).
Fleer et al., "Septicemia due to Coagulase-negative Staphylococci in a Neonatal Intensive Care Unit: Clinical and Bacteriological Features and Contaminated Parenteral Fluids as a Source of Sepsis," *Pediatr. Infect. Dis.*, 2:426-431 (1983).

Fischer et al., "Diminished Bacterial Defenses with Intralipid," *The Lancet*, 2:819-820 (1980).

Yoshida et al., "Immunological Response to a Strain of *Staphylococcus epidermidis* in the Rabbit: Production of Protective Antibody," *J. Med. Microbiol.*, 11:371-377 (1977).

Yoshida et al., "Mouse Virulent Strain of *Staphylococcus epidermidis,*" *Jap. J. Microbiol.*, 20:209-217 (1976).

West et al., "Detection of Anti-teichoic Acid Immunoglobulin G Antibodies in Experimental *Staphylococcus epidermidis* Endocarditis," *Infect. and Immun.*, 42:1020-1026 (1983).

Espersen et al., "Enzyme-linked Immunosorbent Assay for Detection of *Staphylococcus epidermidis* Antibody in Experimental *S. epidermidis* Endocarditis," *J. Clin. Microbiol.*, 23:339-342 (1986).

Fischer, "Therapeutic Uses of Intravenous Gammaglobulin for Pediatric Infections," *Pediatric Clinics of North America*, 35:517-533 (1988).

Biotechnology Newswatch, A. McGraw-Hill Production, pp. 2-3, Oct. 4, 1993.

Ichiman et al., Induction of Resistance with Heat-Killed Unencapsulated Strains of *Staphylococcus epidermidis* Against Challenge with Encapsulated Strains of *Staphylococcus epidermidis*, Microbiol. Immunol., vol. 33 (4), pp. 277-286, (1989).

Yang et al., "Mechanisms of Bacterial Opsonization by Immune Globulin Intravenous: Correlation of Complement Consumption with Opsonic Activity and Protective Efficacy," *The Journal of Infectious Diseases*, 159:701-707 (1989).

Bronswijk et al., "Heterogeneity In Opsonic Requirements of *Staphylococcus epidermidis*: Relative Importance of Surface Hydrophobicity, Capsules and Slime," *Immunology*, 67:81-86 (1989).

I.W. Sutherland, "Separation And Purification Of Bacterial Antigens," *Handbook of Experimental Immunology*, D.M. Weir, ed., chapter 2, pp. 2.1-2.17 (1978).

Naumova et al., "The Occurrence of Teichoic Acids in Streptomycetes," *Chemical Abstracts*, 93, Abstract No. 3555r (1980).

Espersen et al., "*Staphylococcus aureus*," pp. 127-143, *in Antigen Detection to Diagnose Bacterial Infections*, R.B. Kohler ed., vol. 2, (CRC Press, Inc., Boca Raton, Florida, 1986).

A. Fattom et al., Capsular Polysaccharide Serotyping Scheme for *Staphylococcus epidermidis*, Journal of Clinical Microbiology, vol. 30, No. 12, pp. 3270-3273 (Dec. 1992).

K. Yoshida et al., Cross Protection Between a Strain of *Staphylococcus epidermidis* and Eight Other Species of Coagulase-Negative Staphylococci, Can. J. Microbiol., vol. 34, pp. 913-915 (1988).

Ellis, R.W. "New Technologies for Making Vaccines" In: Vaccines, Plotkin and Mortimer Eds., W.B. Saunders Co. 1988, pp. 568-575.

Boslego, J.W. et al., "Gonorrhea Vaccines", In: Vaccines and Immunotherapy, Cryz Ed., Pergamon Press, 1991, pp. 211-223.

Bio: Critical Synergy: The Biotechnology Industry and Intellectual Property Protection, Biotechnology Industry Organization, Oct. 17, 1994, p. 101.

Smith, D.G. et al., Infection and Immunity 59(2) :617-624, Feb. 1991.

Patrick, C.C. et al., J. Clin. Microbiol. 28(12) :2757-2760, Dec. 1990.

Bonnerjea, J. et al., Bio/Technology 4:954-958, 1986.

Fattom, A. et al., Infection and Immunity 58(7) :2367-2374, Jul. 1990.

Timmerman et al., Characterisation and Functional Aspects of Monoclonal Antibodies Specific for Surface Proteins of Coagulase-Negative Staphylococci, J. Med. Microbiol., vol. 35, pp. 65-71 (1991).

Shaio et al., "Effect of Immune Globulin Intravenous on Opsonization of Bacteria by Classic and Alternative Complement Pathways in Premature Serum", Pediatric Research, 25:634 (1989).

Ahmed et al., Preparation and Efficacy of Staphylococcal Vaccine by Sequential Release of Antigen from Solvent Treated Bacteria, *Soc. appl. Bacter.* 67: xv(1989).

Baird-Parker, The Basis for the Present Classification of Staphylococci and Micrococci, Recent Advances in Staphylococcal Research, *Ann. N.Y. Acad. Sci.* 236: 7-14 (W. Yotis, ed. 1974).

Baker et al., Intravenous Immune Globulin for the Prevention of Nosocomial Infection in Low Birth Weight Neonates, *New Eng. J. Med.* 327: 213-219 (1992).

Campbell, Monoclonal Antibodies and Immunosensor Technology, *Laboratory Techniques in Biochemistry and Molecular Biology 23*, Chapter 1, pp. 1-49 (1993).

Carozzi et al., Response of CAPD Patients with a High Incidence of Peritonitis to Intraperitoneal Immunoglobulin Therapy, *Trans. Am. Soc. Artif. Intern. Organs.* 34: 635-639 (1988).

Chugh et al., Adherence of *Staphylococcus epidermidis* to Fibrin-Platelet Clots In Vitro Mediated by Lipoteichoic Acid, *Infect. and Immun.* 58: 315-319 (1990).

Cieslak et al., Post-Immunization Antibodies to *S. epidermidis* are Broadly Reactive and Opsonic, *Ped.Rreasearch* 31: 275A (1992).

Clapp et al., Use of Intravenously Administered Immune Globulin to Prevent Nosocomial Sepsis in Low Birth Weight Infants: Report of a Pilot Study, *J. Pediatr.* 115: 973-978 (1989).

Dick et al., Glycoconjugates of Bacterial Carbohydrate Antigens, *Contrib. Microbiol & Immunol.* 10: 48-114 (1989).

Doyle et al., Soluble Macromolecular Complexes Involving Bacterial Teichoic Acids, *J. Bacteriol.* 124: 341-347 (1975).

Fanaroff et al., A Controlled Trial of Intravenous Immune Globulin to Reduce Nosocomial Infections in Very-Low-Birth-Weight Infants, *New Eng. J. Med.* 330: 1107-1113 (1992).

Fischer et al., Opsonic antibodies to *Staphylococcus epidermidis*: in vitro and in vivo studies using human intravenous uimmune globulin, *J. Inf. Dis.* 169: 324-329 (1994).

Gunn, Comparative Virulence of Human Isolates of Coagulase-Negative Staphylococci Tested in an Infant Mouse Weight Retardation Model, *J. Clin. Microbiol.* 27: 507-511 (1989).

Harlow et al., Monoclonal Antibodies, *Antibodies: A Laboratory Manual* Cold Spring Harbor Laboratory, Chapter 6, 139-243 (1988).

Ichiman et al., Cross Protection of Mice with the Smith Diffuse Strain of *Staphylococcus aureus* versus a type Ia Strain of Group B Streptococci, *Can. J. Microbiol.* 28: 726-732 91982).

Jackson et al., Monoclonal Antibodies to Immunodeterminants of Lipoteichoic Acids, *Infect. & Immun.* 43: 800-03 (1984).

Kotani et al., Immunoadjuvant Activities of the Enzymatic Digests of Bacterial Cell Walls Lacking Immunoadjuvancy by Themselves, *Biken Journal* 20: 87-90 (1977).

Losnegard et al., Immunochemical Studies on Polysaccharides from *Staphylococcus epidermidis*, *Acta Path. Microbiol. Scand.* 58: 493-500 (1963).

Mancuso et al., Anti-lipoteichoic Acid Antibodies Enhance Release of Cytokines by Monocytes Sensitized with Lipoteichoic Acid, *Infect. & Imm.* 62: 1470-73 (1994).

Modun et al., A Preparation of *Staph. epidermidis* Vaccine by Enzymatic Digestion of Bacterial Cells, *J. Appl. Bacteriol.* 67:xv-xvi (1989).

Naumora et al., The Occurrence of Teichoic Acids in Steptomycetes, *Arch. Microbiol.* 126: 71-75 (1980).

Oeding et al., Classification of Coagulase-Negative Staphylococci in the Diagnostic Laboratory, *ACTA Path. Microbiol. Scand.* 85:136-140 (1977).

Osland et al., Imunochemical Analysis of the Teichoic Acid from *Staphylococcus hyicus*, *ACTA Path. Microbiol. Scan.* 87: 165-169 (1979).

Osland et al., Imunochemical Analysis of the Teichoic Acid from *Staphylococcus simulans*, *ACTA Path. Microbiol. Scan.* 88: 121-23 (1980).

Poole-Warren et al., The Role of Vaccination in the Prevention of Staphylococcal Peritonitis in Continuous Ambulatory Peritoneal Dialysis, *Per. Dial. Int.* 13:176-177 (1993).

Raynor et al., Lipoteichoic Acid Inhibition of Phagocytosis of *Staphylococcus aureus* by Human Polymorphonuclear Leukocytes, *Clin. Immunol. & Immunopath.* 19: 181-89 (1981).

Robbins et al., Polysaccharide-Protein Conjugates: A New Generation of Vaccines, *J. Infect. Dis.* 161:821-832 (1990).

Roitt, *Essential Immunology*, Blackwell Scientific Publication, Oxford England, Chap. 4, pp. 55-68 (1988).

Santos et al., Functional Leukocyte Administration in Protection Against Experimental Neonatal Infection, *Pediatr. Res.* 14: 1408-1410 (1980).

Siber, Immune Globulin to Prevent Nocosomial Infections, *New Eng. J. Med.* 327:269-271 (1992).

Takeda et al., Protection Against Endocarditis Due to *Staphylococcus epidermidis* by Immunization with Capsular Polysaccharide/Adhesin, *Circulation* 84: 2539-46 (1991).

Tojo et al., Isolation and Characterization of a Capsular Polysaccharide Adhesin from *Staphylococcus epidermidis*, *J. Infect. Dis.* 157:713-722 (1988).

Verbrugh et al., Opsonic Recognition of Staphylococci Mediated by Cell Wall Peptidoglycan: Antibody-Independent Activation of Human Complement and Opsonic Activity of Peptidoglycan Antibodies, *J. Immunol.* 124: 1167-1173 (1980).

Verhoef et al., Opsonic Requirements for Staphylococcal Phagocytosis, *Immunology* 33:191-197 (1977).

Wadström, Molecular Aspects of Bacterial Adhesion, Colonization, and Development of Infections Associated with Biomaterials, *J. Invest. Surgery* 2:353-360 (1989).

Weisman et al., Intravenous Immune Globulin Prophylaxis on Late-Onset Sepsis in Premature Neonates, *J. Ped.* 125:922-930 (1994).

Wergeland et al., Antibodies to Various Bacterial Cell Wall Peptidoglycans in Human and Rabbit Sera, *J. Clin.Microbiol.* 25: 540-545 (1987).

Wilkinson, Immunochemistry of Purified Polysaccharide Type Antigens of Group B Streptococcal Types Ia, Ib, and Ic, *Infect. Immun.* 11: 845-852 (1975).

Williams et al., Protein Antigens of *Staphylococcus epidermidis* Grown Under Iron-Restricted Conditions in Human Peritoneal Dialysate, *FEMS Microbiol. Ltrs.* 50:29-33 (1988).

Yoshida et al., Staphylococcal Capsular Vaccine for Preventing Mastitis in Two Herds in Georgia, *J. Dairy Sci.* 67: 620-627 (1984).

Yoshitomi, Serological Differentiation of Strains of *Staphylococcus epidermidis* by the Soft Agar Technique, *St. Marianna Med. J.* 17:166-174 (1989).

Gonzalez and Hill, The Current Status of Intravenous Gammaglobulin Use in Neonates, *J. Ped. Infect. Dis.* 8: 315-22 (1989).

NIH Consensus Conference, Intravenous Immunoglobulin: Prevention and Treatment of Disease, *JAMA* 264: 3189-93 (1990).

Wheat, Analysis of Hexosamines in Bacterial Polysaccharides by Chormatographic Procedures, *Methods in Enzymology* 8: 60-78 (1966).

\* cited by examiner

ISOLATED BROADLY REACTIVE OPSONIC IMMUNOGLOBULIN FOR TREATING A PATHOGENIC COAGULASE-NEGATIVE STAPHYLOCOCCUS INFECTION

CROSS REFERENCE TO RELATED APPLICATIONS

This is a division of application Ser. No. 08/308,495 filed Sep. 21, 1994 now abandoned which is a continuation-in-part of application Ser. No. 08/033,476, filed Mar. 18, 1993, abandoned, which is a continuation-in-part of application Ser. No. 07/854,027 filed Mar. 19, 1992, abandoned, which is a continuation-in-part of application Ser. No. 07/804,317 filed Feb. 25, 1992, abandoned, which is a continuation of application Ser. No. 07/601,089 filed Oct. 22, 1990, abandoned.

GOVERNMENT INTEREST

The invention described herein may be manufactured, licensed, and used by or for governmental purposes without the payment of any royalties to the inventor.

FIELD OF THE INVENTION

This invention describes immunoglobulin, including polyclonal and monoclonal antibodies, and isolated antigen useful for preventing, diagnosing, and treating staphylococcal infections. This invention also describes a lethal animal model useful for determining the efficacy of pharmacological compositions against infectious agents including, but not limited to, staphylococcal infections.

BACKGROUND OF THE INVENTION

Over the last two decades, staphylococcal infections have become important causes of human morbidity and mortality, particularly in hospitalized patients. Because of their prevalence on the skin and mucosal linings, staphylococci are ideally situated to produce infections, both localized and systemic. Debilitated or immunosuppressed patients are at extreme risk of systemic infection.

The *staphylococcus* species most frequently pathogenic in humans are *Staphylococcus aureus* and *Staphylococcus epidermidis*. Each species includes a number of serotypes. Both groups have developed resistance to antibiotics, the current treatment of choice.

In recent years, *S. epidermidis* has become a major cause of nosocomial infection in patients having treatments comprising placing implants into the body, such as cerebrospinal fluid shunts, cardiac valves, vascular catheters, and joint prostheses. *S. epidermidis* is also a common cause of postoperative wound infections and peritonitis in patients with continuous ambulatory peritoneal dialysis. One form of treatment for kidney failure entails the introduction of large volumes of peritoneal dialysis fluid into the peritoneal cavity, a treatment carrying a risk of frequent and recurrent infections.

Patients with impaired immunity and those receiving parenteral nutrition through central venous catheters are at high risk for developing *S. epidermidis* sepsis (C. C. Patrick, *J. Pediatr.*, 116:497 (1990)). In particular, *S. epidermidis* has become a common cause of neonatal nosocomial sepsis, and is now the most common cause of bacteremia in the neonatal intensive care unit setting. Infections frequently occur in premature infants receiving parenteral nutrition, which can be a direct or indirect source of contamination. Such infections are difficult to treat for a variety of reasons. For example, resistance to antibiotics is common. In one study, the majority of staphylococci isolated from blood cultures of septic infants were multiply resistant to antibiotics (Fleer et al., *Pediatr. Infect. Dis.*, 2:426 (1983)). Stimulation of the immune system provides little relief because such infants have impaired immunity resulting from deficiencies in antibodies, complement, and neutrophil function. Moreover, lipid infusion, which is now a standard ingredient of parenteral nutrition therapy, further impairs the already poor infant immune response to bacterial infection (Fischer et al., *Lancet*, 2:819 (1980)). Infection with *S. epidermidis* in these patients increases morbidity and mortality, and adds intensive care days that markedly increase medical costs.

Supplemental immunoglobulin therapy has been shown to provide some measure of protection against certain encapsulated bacteria, such as *Hemophilus influenzae* and *Streptococcus Pneumoniae*. Infants deficient in antibody are susceptible to infections from these bacteria, and thus, bacteremia and sepsis resulting from infection are common. When anti-Streptococcal and anti-*Hemophilus* antibodies are present, they provide protection by promoting clearance of the respective bacteria from the blood. In the case of antibody specific for *staphylococcus*, the potential use of supplemental immunoglobulin to prevent or treat infection has been much less clear.

Early studies of staphylococcal infections focused on the potential use of supplemental immunoglobulin to boost peritoneal defenses, such as opsonic activity, in patients receiving continuous ambulatory peritoneal dialysis. Standard intravenous immunoglobulin (IVIG) was shown to have lot to lot variability for opsonic activity to *S. epidermidis* (L. A. Clark and C. S. F. Easmon, *J. Clin. Pathol.*, 39:856 (1986)). In this study, one third of the tested IVIG lots had poor opsonization with complement, and only two out of fourteen were opsonic without complement. Thus, despite the fact that the IVIG lots were made from large plasma donor pools, good opsonic antibody specific for *S. epidermidis* was not uniformly present. Treatment with such immunoglobulin would therefore not provide protection against Staphylococcal infection. This study did not examine whether IVIG could be used to prevent or treat *S. epidermidis* infections or bacterial sepsis.

Recent studies have associated coagulase-negative staphylococci, such as *S. epidermidis*, as the most common species causing bacteremia in neonates receiving lipid emulsion infusion (Freeman et al., *N. Engl. J. Med.*, 323:301 (1990)). The neonates had low levels of opsonic antibody to *S. epidermidis* despite the fact that sera had clearly detectable levels of IgG antibodies to *S. epidermidis* peptidoglycan (Fleer et al., *J. Infect. Dis.*, 2:426 (1985)). This was surprising because anti-peptidoglycan antibodies were presumed to be the principal opsonic antibodies. Thus, while suggesting that neonatal susceptibility to *S. epidermidis* might be related to impaired opsonic activity, these studies also suggested that many antibodies directed against *S. epidermidis* are not opsonic and would not be capable of providing protection when given passively to neonates. Moreover, the antigens responsible for inducing opsonic antibodies were not identified.

Recently, an antigen binding assay was used to analyze IgG antibody to *S. epidermidis* in patients with uncomplicated bacteremia and in patients with bacteremia and endocarditis (Espersen et al., *Arch. Intern. Med.*, 147:689 (1987)). This assay used an ultrasonic extract of *S. epidermidis* to identify *S. epidermidis* specific IgG. None of the patients with uncomplicated bacteremia had IgG antibodies specific for *S. epidermidis*. These data suggest that IgG does not provide effective eradication of *S. epidermidis* from the blood. In addition, 89% of bacteremic patients with endocarditis developed high levels of IgG to *S. epidermidis*. In these patients, IgG was not protective since high levels of IgG antibody were associated with serious bacteremia and endocarditis. Based on these studies, the protective role of IgG in *S. epidermidis* sepsis and endocarditis was questionable, especially in the presence of immaturity, debilitation, intralipid infusion, or immunosuppression.

The role of antibody in immunity to *S. epidermidis* has also been studied in animal models (Kojima et al., *J. Infect. Dis.*, 162:435–441 (1990); and Yoshida et al., *J. Appl. Bacteriol.*, 47:299–301 (1979)). Animal studies that demonstrated immunoglobulin protection against staphylococcal infections have shown strain specificity by enzyme-linked immunosorbent assays (ELISA). These studies utilized normal adult mice having a mature immune system in protection studies, and therefore do not mimic the disease observed in humans. Studies using mature animals with normal immunity typically comprise administering to the animals unusually virulent strains or overwhelming-challenge doses of bacteria. This does not mimic infection in humans because human patients are generally immunologically immature or debilitated. Human patients can also have somewhat indolent infections with low virulence pathogens, such as *S. epidermidis*, with death usually attributable to secondary complications rather than the bacterial infection. Models using unusual strains or overwhelming bacterial doses generally induce rapid fulminant death.

These factors are important since antibodies generally work in concert with the host cellular immune system (neutrophils, monocytes, macrophages, and fixed reticuloendothelial system). The effectiveness of antibody therapy may therefore be dependent on the functional immunologic capabilities of the host. To be predictive, animal models must closely mimic the clinical condition in which the infection occurs and capture the setting for therapy.

Prior animal studies have yielded inconsistent results. One animal model used an unusually virulent strain of *S. epidermidis*. Infected mature mice developed 90 to 100% mortality within 24 to 48 hours (Yoshida et al., *Japan. J. Microbiol.*, 20:209 (1976)). Antibody to *S. epidermidis* surface polysaccharide was protective in these mice, with protection occurring for an IgM fraction but not an IgG fraction (K. Yoshida and Y. Ichiman, *J. Med. Microbiol.*, 11:371 (1977)).

This model presents a pathology very different from that typically seen in infected patients. Intraperitoneally-challenged mice developed symptoms of sepsis within minutes of receiving the injection and died in 24 to 48 hours. This pathology is not observed in *staphylococcus*-infected humans. The highly virulent strain of *S. epidermidis* may represent an atypical type of infection. Moreover, isolates of *S. epidermidis* from infected humans did not kill mice in this model.

In 1987, animal studies were extended to include the evaluation of antibodies in human serum against selected virulent strains of *S. epidermidis* (Ichiman et al., *J. Appl. Bacteriol.*, 63:165 (1987)). In contrast to previous data, protective antibody was found in the IgA, IgM, and IgG immunoglobulin fractions. A definitive role for any single class of immunoglobulin (IgG, IgM, IgA) could not be established.

In this animal model, mortality was determined for normal adult mice. Death was considered to be related to the effect of specific bacterial toxins, not bacteremia sepsis (Yoshida et al., *Japan J. Microbiol.*, 20:209 (1976)). Most clinical isolates did not cause lethal infections, and quantitative blood cultures were not done. This study provided little insight as to whether antibody could successfully prevent or treat *S. epidermidis* sepsis in immature or immunosuppressed patients.

In a later animal study, serotype specific antibodies directed against *S. epidermidis* capsular polysaccharides were tested. Results showed that serotype-specific antibodies were protective, but that each antibody was directed against one particular serotype as measured by ELISA (Ichiman et al., *J. Appl. Bacteriol.*, 63:165 (1987)). Protection was equally serotype specific. Protection against heterologous strains did not occur. In addition, it was concluded that protection was afforded by the IgM antibody.

In short, there has been no compelling evidence that IVIG, which contains only IgG, could be effective to treat and prevent *S. epidermidis* infections or sepsis, particularly where patients are immature or immune suppressed, or where multiple *S. epidermidis* serotypes are involved. Thus, for example, a recent and extensive review of the pathogenesis, diagnosis, and treatment of *S. epidermidis* infections does not include immunoglobulin as a potential prophylactic or therapeutic agent (C. C. Patrick, *J. Pediatr.*, 116:497 (1990)).

An animal model that mimics human *S. epidermidis* infections has not been developed, particularly for humans that are immature or immune suppressed. This is critical because these patients have low levels of complement as well as impaired neutrophil and macrophage function. Thus, even if opsonic activity of immunoglobulin may appear adequate under optimal conditions in vitro, protection may not occur in patients such as newborn babies or cancer patients. Moreover, previous models are unsatisfactory in that they used animals which did not possess similar risk factors as the typical high-risk human patient.

Although coagulase negative staphylococci (CNS) are significant as nosocomial pathogens, no effective method to prevent CNS infections has been developed. The current preferred treatment of choice for the prevention and cure of staphylococcal infections in humans is antibiotic therapy. Although new antibiotics are constantly being developed, it has become increasing clear that antibiotic therapy alone is insufficient. Data regarding passive vaccinations with immunoglobulin is at best unclear. The animal models on which this therapy has been attempted bear little relationship to human infections and as yet, have produced no definitive solutions. In summary, there is a need in the art for an effective treatment for staphylococci infections.

SUMMARY OF THE INVENTION

The present invention overcomes the problems and disadvantages associated with current strategies and provides a new therapy for the treatment and prevention of staphylococcal infections. This invention describes broadly reactive opsonic immunoglobulin reactive with common staphylococcal antigens from which vaccines, pharmaceutical compositions, and diagnostic aids can be created for the treatment and prevention of staphylococcal infections in both man and animals.

In particular, the invention describes a common surface protein present on several *S. epidermidis* strains having different serotypes. Although this surface protein is from a single *S. epidermidis* strain, it induces broadly reactive and opsonic antibodies. Thus, the protein is useful for screening plasma to make opsonic immunoglobulin that is broadly reactive across all three serotypes of *S. epidermidis*, and for a vaccine to induce active immunity to *S. epidermidis*.

The invention also describes broadly reactive and opsonic immunoglobulin induced by a Serotype II *S. epidermidis* capsular polysaccharide. The immunoglobulin is broadly reactive against all staphylococci, including *S. epidermidis* and other coagulase negative *staphylococcus*, as well as *S. aureus*. This suggests that broadly protective immunity could be directed against capsular polysaccharides and that the eliciting antigen provides an important human virulence factor that crosses staphylococcal species.

In preferred embodiments of both aspects of the invention, the immunoglobulin is reactive in an assay with a preparation of *S. epidermidis* (Hay, ATCC 55133). Thus, this one strain provides a single step screen for immunoglobulin production. Moreover, immunization with this one strain, or with antigens purified from the single strain, induces opsonic antibodies broadly reactive across *S. epidermidis* serotypes and staphylococcal species. Thus, this organism would be useful for identifying and purifying vaccine antigens.

The invention includes immunoglobulin found in individual samples or pools of serum, plasma, whole blood, or tissue; isolated immunoglobulin which may be polyclonal antibodies or monoclonal antibodies; methods for making polyclonal and monoclonal antibodies; isolated antigen; methods for making isolated antigen; pharmaceutical compositions comprising isolated immunoglobulin or isolated antigen; and methods for the prophylactic or therapeutic treatment of a patient with pharmaceutical compositions.

Other objects and advantages of the present invention are set forth in the following description. The accompanying drawings and tables, which constitute a part of the disclosure, illustrate and, together with this description, explain the principle of the invention.

BRIEF DESCRIPTIONS OF THE DRAWINGS

FIG. 1: Antibody titers of human plasma tested for binding to *S. epidermidis* serotypes I, II, III, and Hay.

Figure 2:
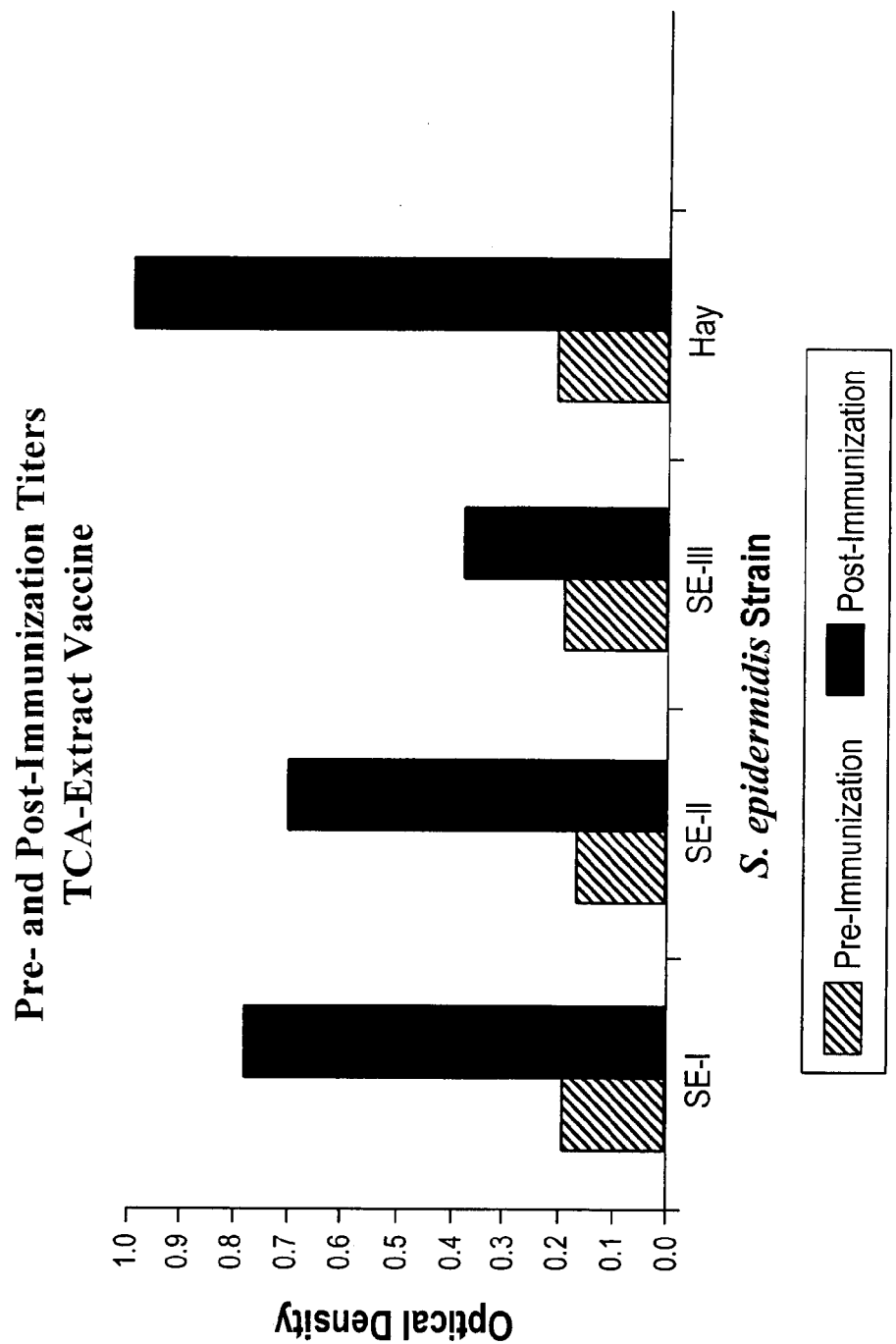

FIG. 2: Pre- and post-immunization ELISA titers of sera from rabbits immunized with a TCA-extracted antigens of *S. epidermidis* Hay (ATCC 55133) tested for binding to *S. epidermidis* serotypes I, II, III, and Hay.

Figure 3:
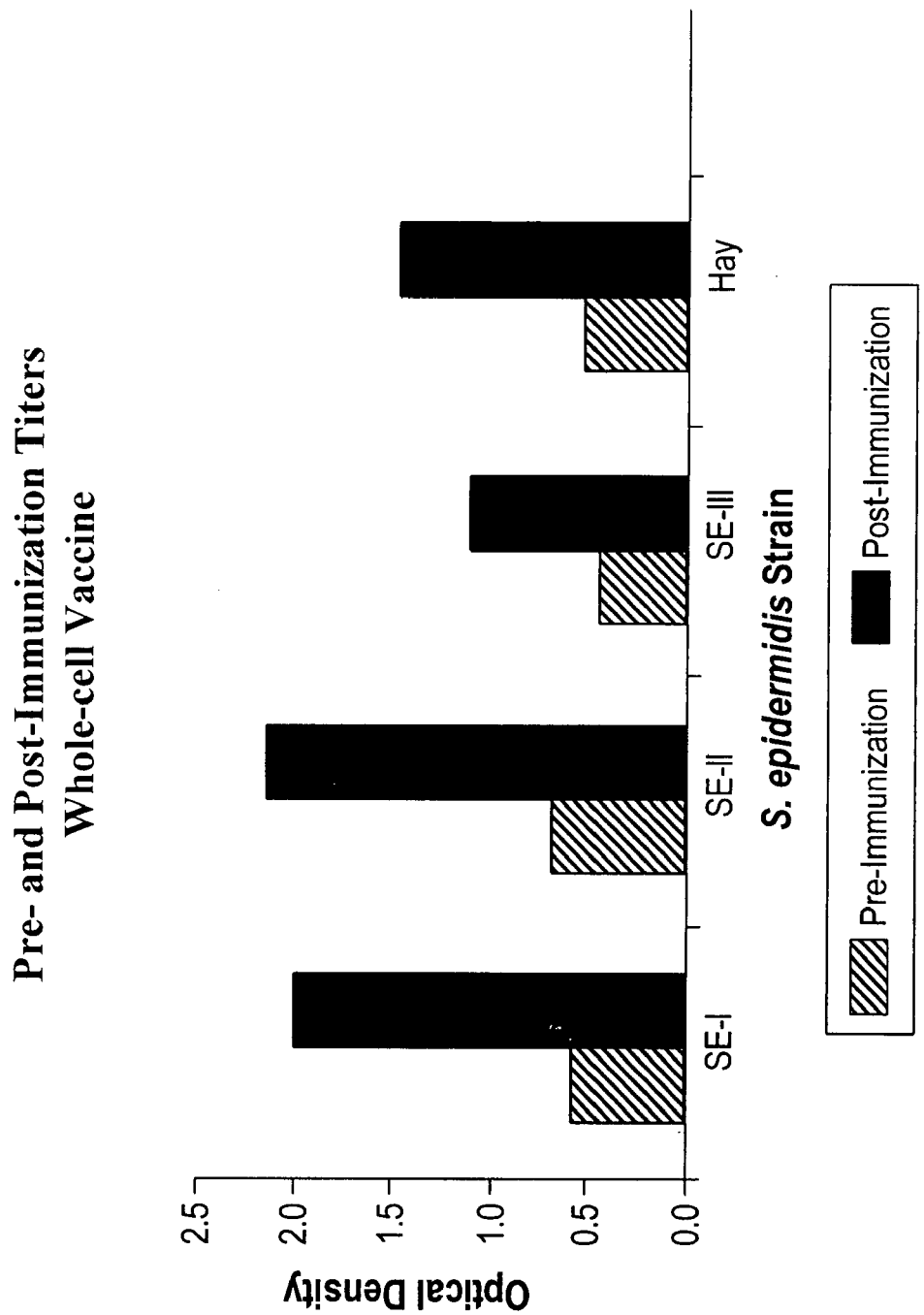

FIG. 3: Pre- and post-immunization ELISA titers of sera from rabbits immunized with a whole cell preparation of *S. epidermidis* Hay (ATCC 55133) tested for binding to *S. epidermidis* serotypes I, II, III, and Hay.

Figure 4:
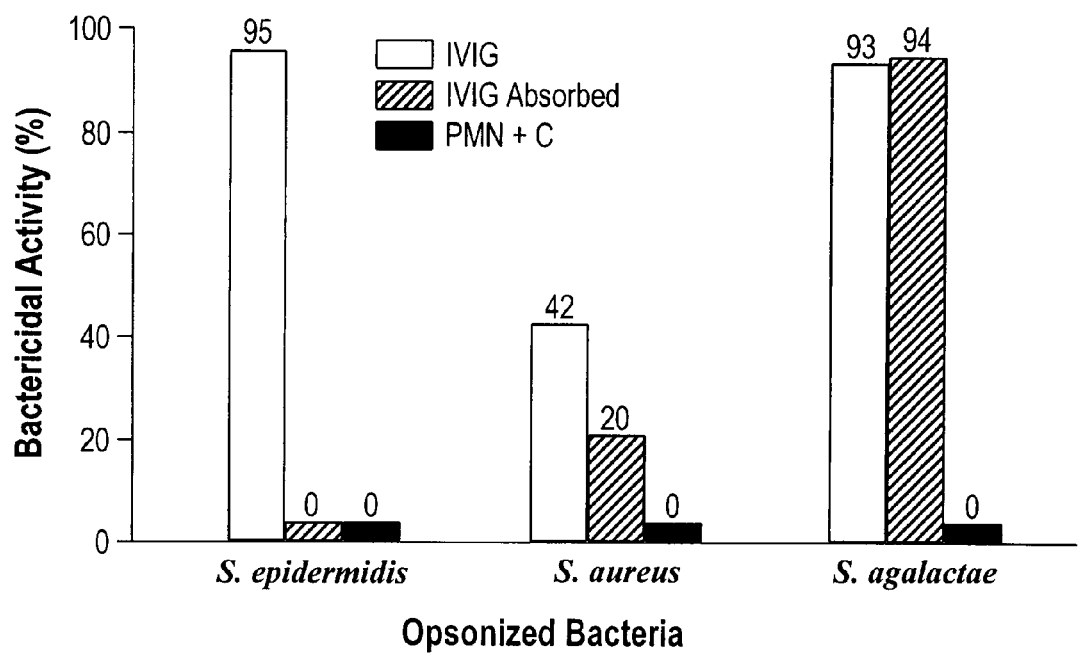

FIG. 4: Effect of absorption of immunoglobulin with *S. epidermidis* on opsonization. Neutrophil mediated opsonization assay of *S. epidermidis*, *S. aureus*, and *Streptococcus agalactiae* organisms using immunoglobulin selected for the ability to bind to a preparation of *S. epidermidis*, and selected immunoglobulin preabsorbed with a preparation of *S. epidermidis*. Negative control is neutrophils plus complement alone.

Figure 5:
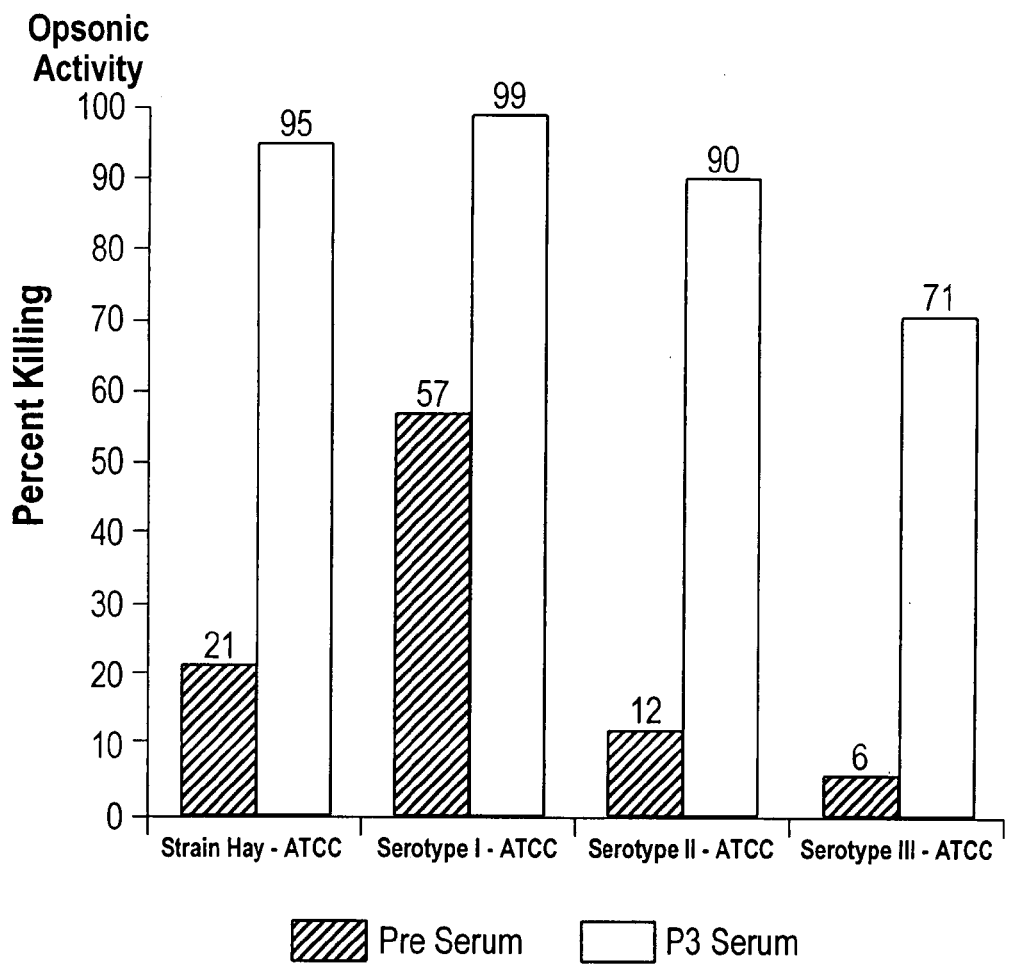

FIG. 5: opsonic antibody response (opsonic activity) to *S. epidermidis* Serotypes I, II, III, and Hay measured as percent bactericidal response to rabbit serum pre- and post-immunization with a TCA-extracted antigen preparation of *S. epidermidis* Hay (ATCC 55133).

Figure 6:
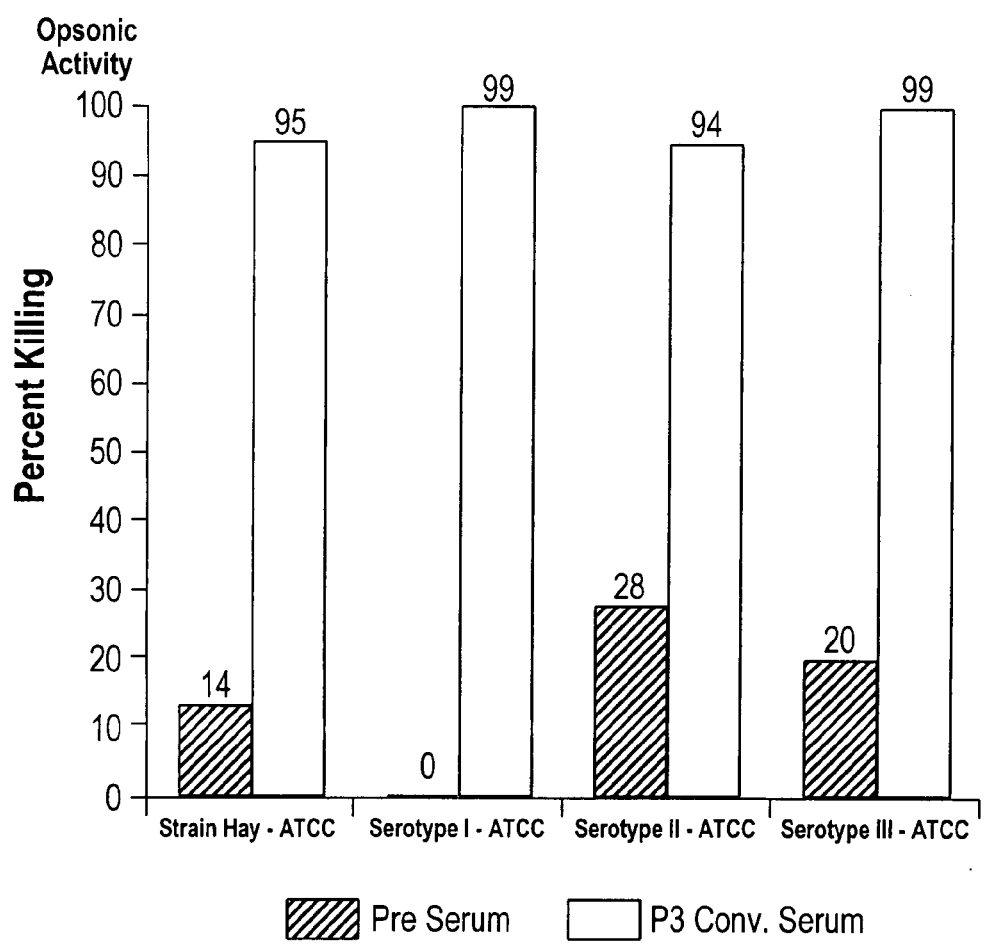

FIG. 6: opsonic antibody response (opsonic activity) to *S. epidermidis* Serotypes I, II, III, and Hay measured as percent bactericidal response to rabbit serum pre- and post-immunization with a whole cell preparation of *S. epidermidis* Hay (ATCC 55133).

Figure 7:
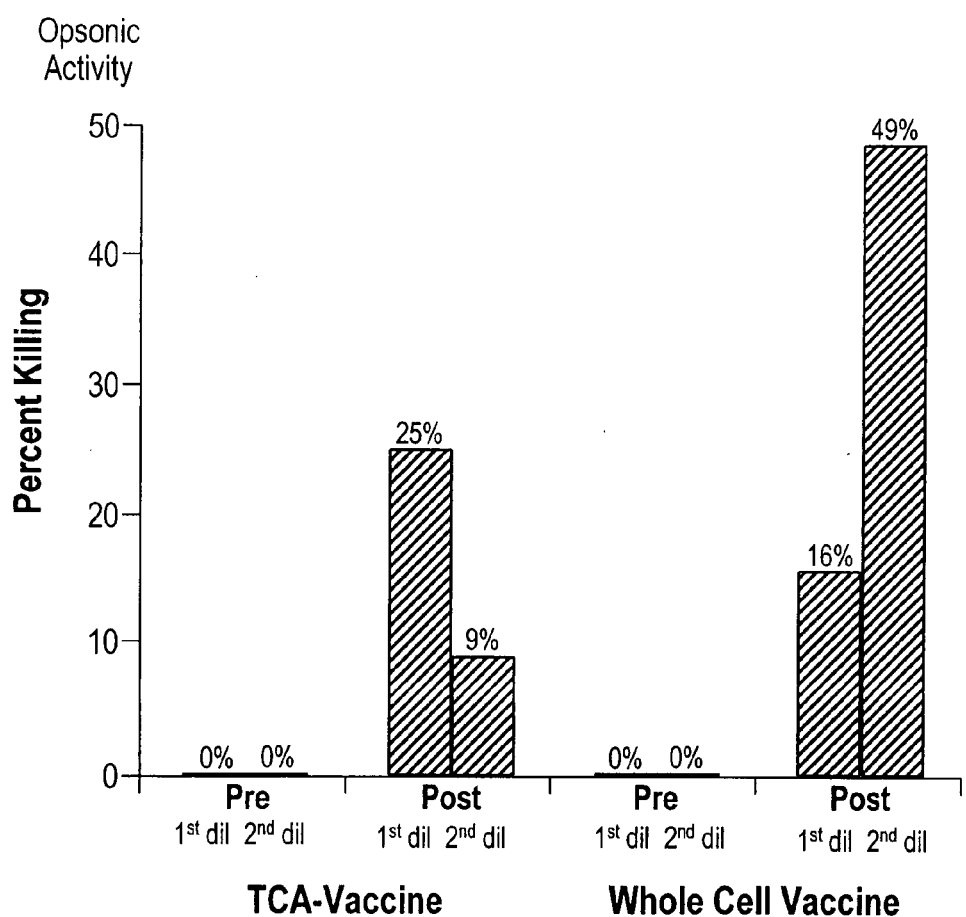

FIG. 7: Opsonic activity of pre- and post-immunization serum with TCA-extracted antigens or whole cell preparation of *S. epidermidis* Hay (ATCC 55133) against *S. aureus* type 5. Opsonic assays were calculated using two dilutions of the reaction mixture prior to subculturing on to solid agar.

Figure 8:
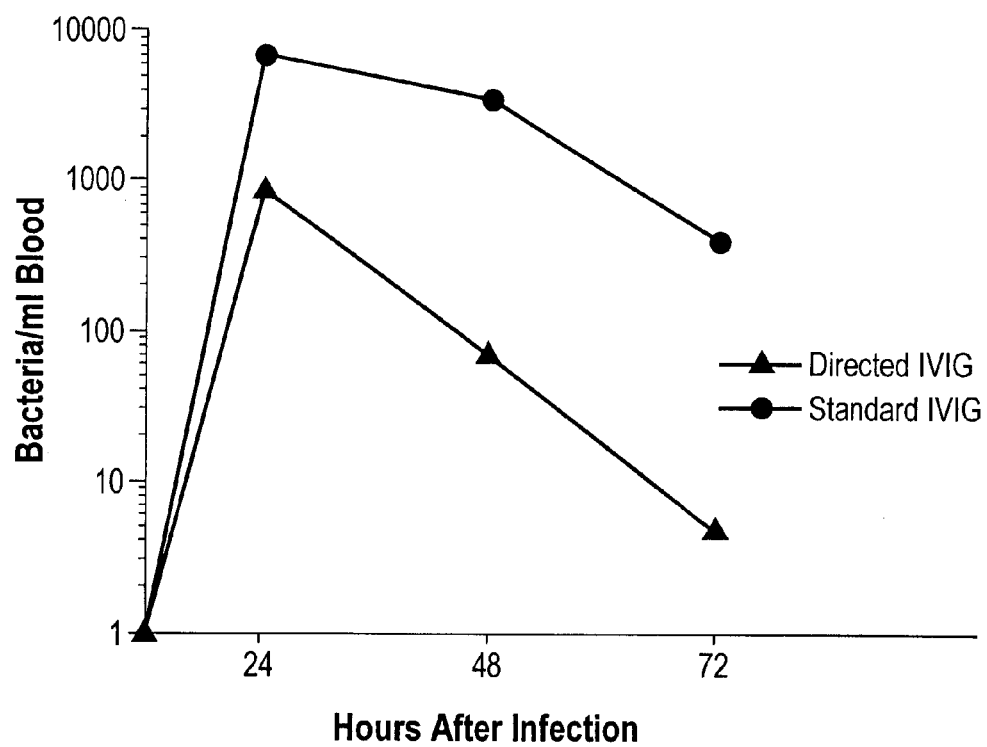

FIG. 8: Effect of high titer vs. low titer IVIG to *S. epidermidis* on clearance of *S. epidermidis* from the blood of animals with *S. epidermidis* sepsis.

Bacteremia levels of *S. epidermidis* were measured in samples of blood from suckling rats treated with either high titer immunoglobulin, selected for the ability to bind to a preparation of *S. epidermidis*, or unselected low-titer immunoglobulin.

Figure 9:
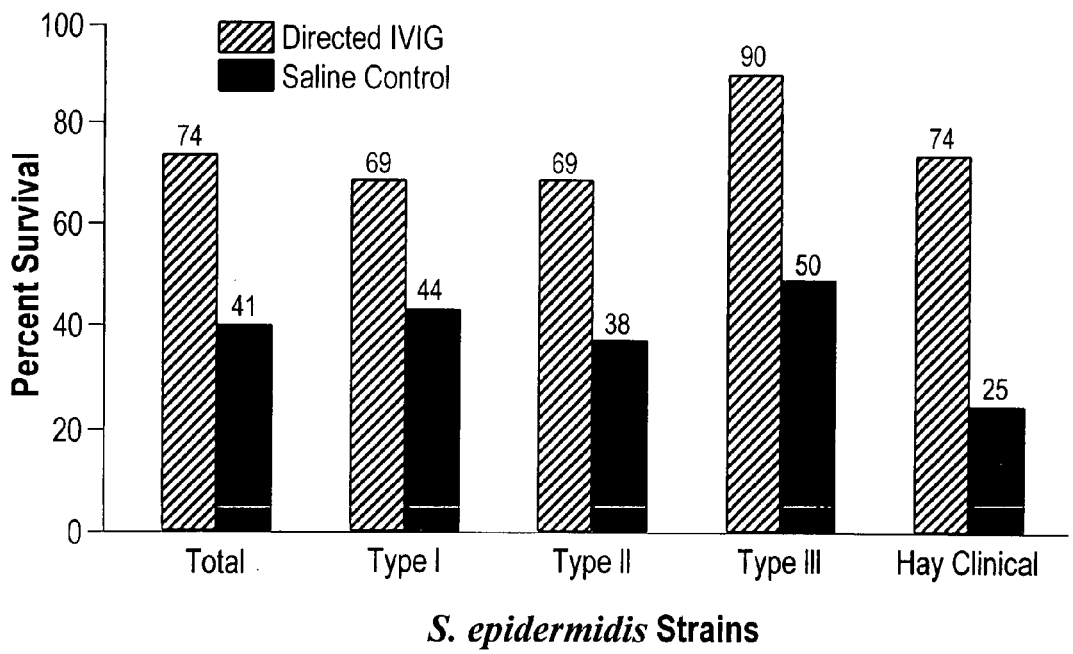

FIG. 9: Effect of directed (selected high-titer) immunoglobulin and saline injections on survival in suckling rats treated with intralipid plus *S. epidermidis*.

Figure 10:
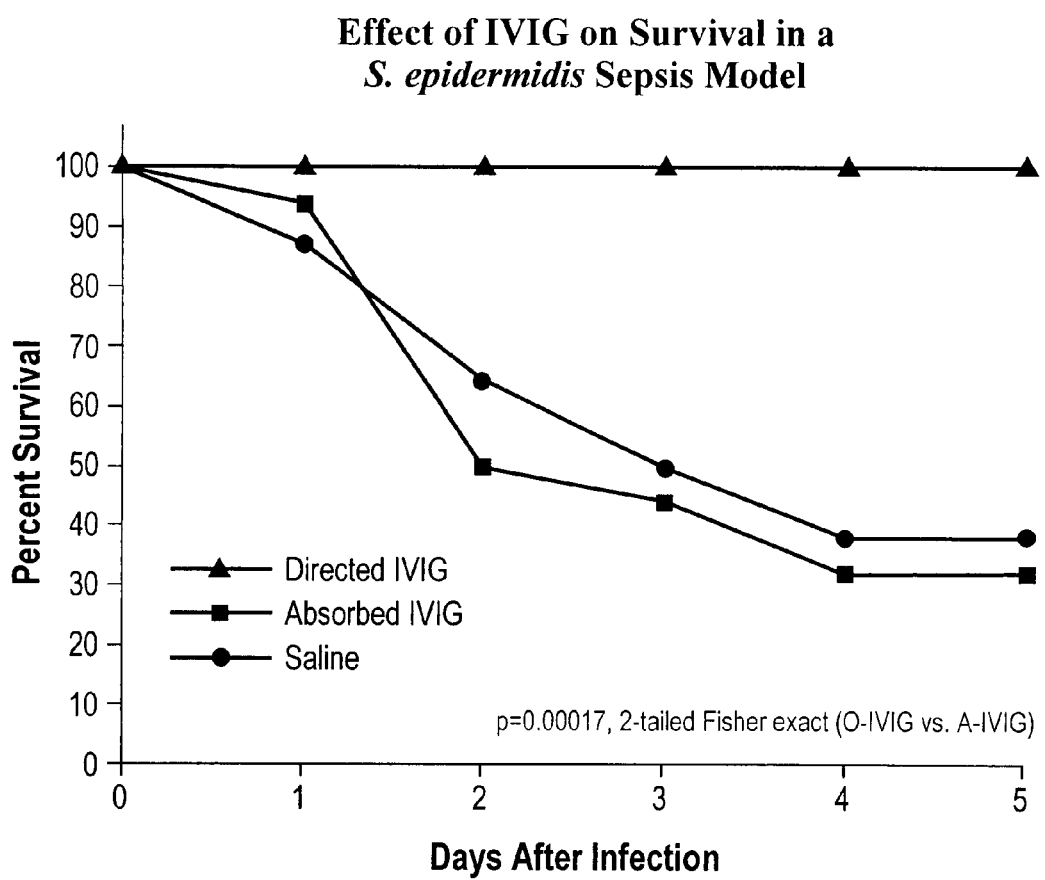

FIG. 10: Effect of directed (selected high-titer) immunoglobulin, directed immunoglobulin preabsorbed with a preparation of *S. epidermidis*, and saline injections on survival in suckling rats treated with intralipid plus *S. epidermidis*.

Figure 11:
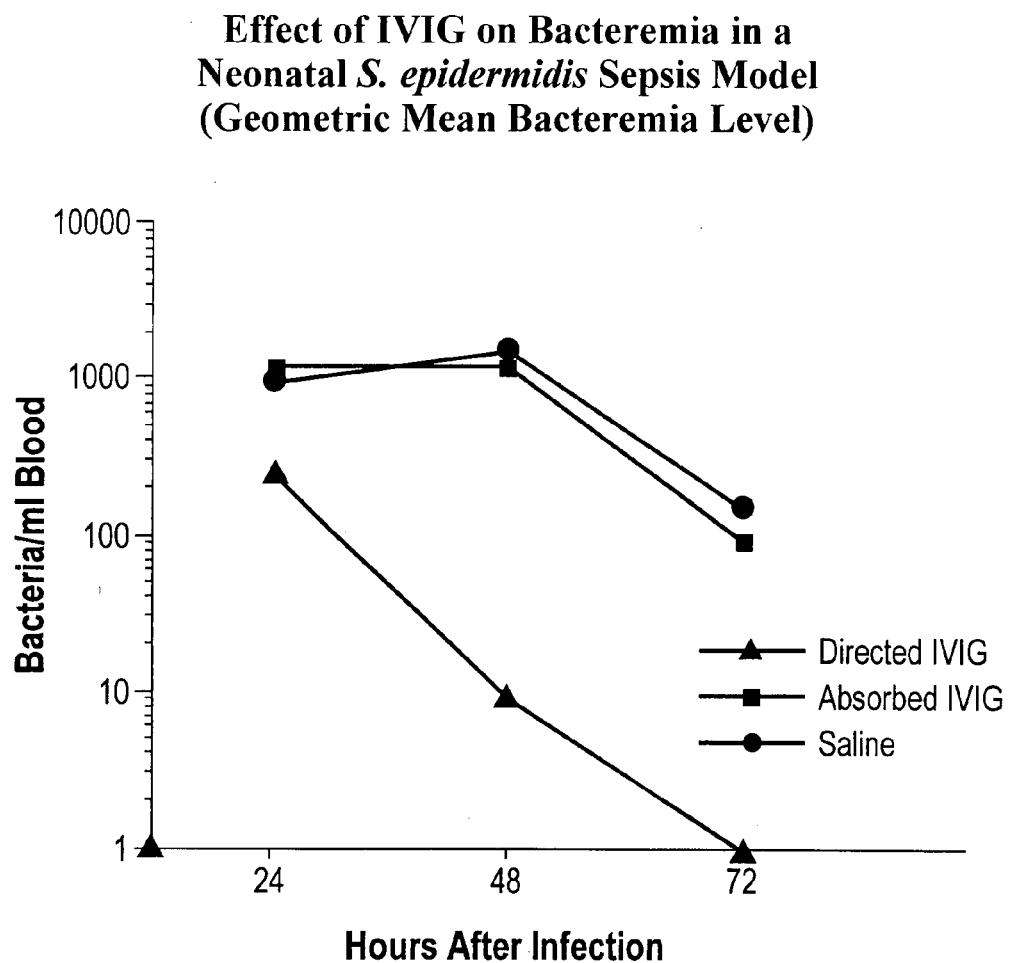

FIG. 11: Effect of directed (selected high-titer) immunoglobulin, directed immunoglobulin preabsorbed with a preparation of *S. epidermidis*, and saline injections on bacteremia levels in the blood of suckling rats treated with intralipid plus *S. epidermidis*.

Figure 12:
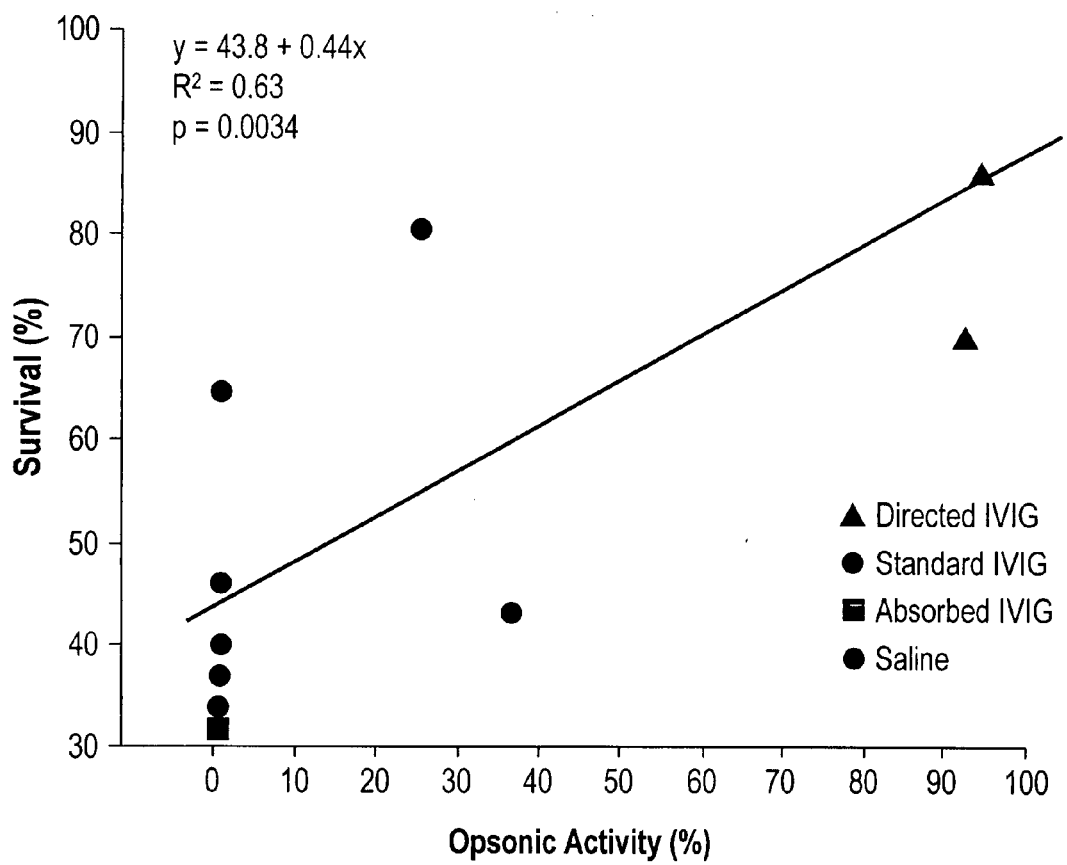

FIG. 12: Relationship between opsonic activity measured in vitro and survival in the suckling rat lethal animal model with directed (selected high-titer) immunoglobulin, unselected low-titer immunoglobulin, directed immunoglobulin preabsorbed with a preparation of *S. epidermidis*, and saline.

Figure 13:
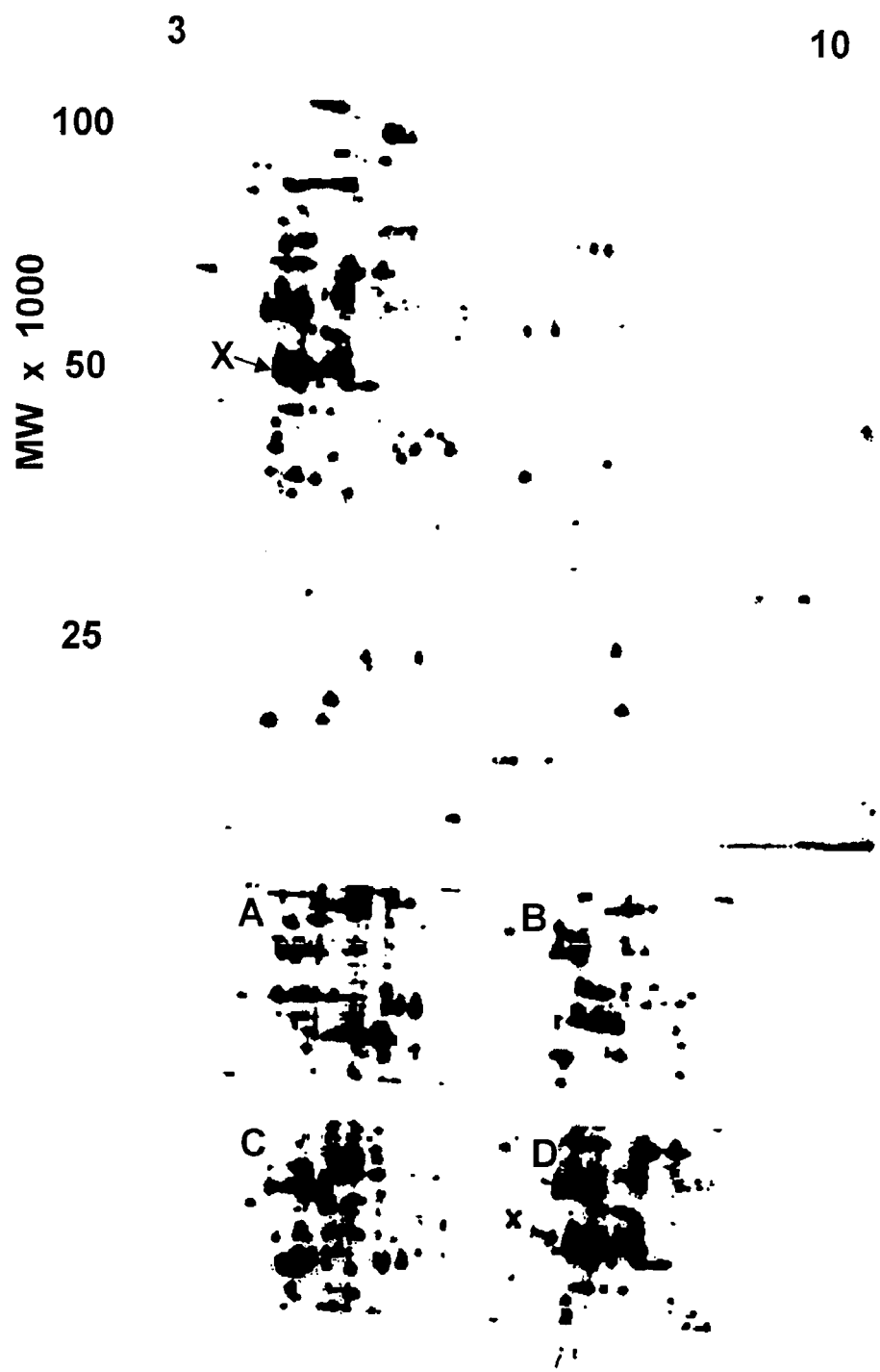

FIG. 13: Samples of *S. epidermidis* were analyzed by two-dimensional gel electrophoresis. A 45–50,000 dalton protein which focuses at a pH of approximately 4.5 was identified on all *S. epidermidis* serotypes.

DESCRIPTION OF PREFERRED EMBODIMENTS

The present invention describes the identification, preparation, and isolation of immunoglobulin and antigen useful for preventing, diagnosing, or treating staphylococcal infections. In particular, the invention provides a single screen with a staphylococcal organism with the proper antigens that will identify broadly reactive and opsonic antibodies to *staphylococcus* that are pathogenic to humans.

In one aspect, the present invention provides broadly opsonic antibodies of *S. epidermidis*, protective across all three serotypes. Such antibodies are induced by a surface protein. Antibodies against this protein are useful opsonins to enhance phagocytosis and eradication of bacteria from a host. The protein can also be used as a tool for screening plasma or immunoglobulins (polyclonal or monoclonal) useful for passive immunotherapy to prevent or treat *S. epidermidis* infections. In addition, this protein is useful for active immunization to induce protection against *S. epidermidis* by vaccination. A particularly useful surface protein has a molecular weight of approximately 45–50 Kd.

In a second aspect, the invention relates to immunoglobulin induced by the serotype II capsular polysaccharide of *S. epidermidis*, which immunoglobulin reacts with human pathogenic staphylococci. The polysaccharide provides an important human virulence marker.

Methods to Identify the Immunoglobulin of the Invention

To identify these broadly opsonic and reactive antibodies, the invention provides a method comprising an assay to identify immunoglobulin (from pooled or individual samples of plasma, serum, whole blood, or tissue, such as placenta) reactive with a preparation of a staphylococcal organism having broadly reactive constituent antigens to identify broadly reactive and opsonic immunoglobulin.

The Preparation

The staphylococcal organism preparation can be any type of preparation, such as intact cells, cells fractionated by chemical or physical means, cell extracts, or purified antigens. Preferably, the preparation is a whole-cell or cell surface extract. It is also preferred that the preparation is from *S. epidermidis* Hay (ATCC 55133) or any other organism bearing the antigens that induce broadly reactive antibodies. A preparation of a staphylococcal organism comprises polysaccharides, proteins, lipids, and other bacterial cell components. Preferably, the preparation comprises polysaccharides and proteins, i.e., a preparation predominantly containing mixtures or combinations of polysaccharides, proteins, and glycoproteins.

A suitable preparation may be prepared by isolating a culture of bacterial cells of *S. epidermidis* Hay (ATCC 55133), suspending the isolated cells in a mixture comprising a solution of trichloroacetic acid (TCA), stirring the mixture at approximately 4° C., centrifuging the mixture and saving the resulting supernatant. This is followed by combining the supernatant with an alcohol, preferably absolute ethanol, incubating the alcohol-supernatant combination at approximately 4° C. to precipitate a preparation, and finally isolating the precipitated preparation.

The Assays

Binding Assays

A preferred assay employs an in vitro assay that identifies opsonic antibody, such as a binding assay or opsonization assay.

In a preferred binding assay, immunoglobulin is reacted with a preparation of a staphylococcal organism. The binding assay is preferably an enzyme-linked immunosorbent assay (ELISA) or a radioimmunoassay (RIA), but may also be an agglutination assay, a coagglutination assay, a calorimetric assay, a fluorescent binding assay, or any other suitable binding assay. The assay can be performed by competitive or noncompetitive procedures with results determined directly or indirectly.

The *staphylococcus* preparation may be fixed to a suitable solid support, such as a glass or plastic plate, well, bead, micro-bead, paddle, propeller, or stick. The solid support is preferably a titration plate. The fixed preparation is incubated with immunoglobulin, which is isolated or in a biological fluid, and the amount of binding determined. A positive reaction occurs when the amount of binding observed for the test sample is greater than the amount of binding for a negative control. A negative control is any sample known not to contain antigen-specific immunoglobulin. Positive binding may be determined from a simple positive/negative reaction or from the calculation of a series of reactions. This series may include samples containing measured amounts of immunoglobulin that specifically bind to the fixed antigen, creating a standard curve from which the amount of antigen-specific immunoglobulin in an unknown sample can be determined. Alternatively, antibody can be fixed to a solid support and immunoglobulin identified by its ability to bind a bacterial preparation bound to the fixed antibodies.

Opsonization Assays

An opsonization assay can be a calorimetric assay, a chemiluminescent assay, a fluorescent or radiolabel uptake assay, a cell-mediated bactericidal assay, or any other appropriate assay which measures the opsonic potential of a substance and identifies broadly reactive immunoglobulin. In an opsonization assay, the following are incubated together: an infectious agent, a eukaryotic cell, and the opsonizing substance to be tested, or an opsonizing substance plus a purported opsonizing enhancing substance. Preferably, the opsonization assay is a cell-mediated bactericidal assay. In this in vitro assay, the following are incubated together: an infectious agent, typically a bacterium, a phagocytic cell, and an opsonizing substance, such as immunoglobulin. Although any eukaryotic cell with phagocytic or binding ability may be used in a cell-mediated bactericidal assay, a macrophage, a monocyte, a neutrophil, or any combination of these cells, is preferred. Complement proteins may be included to observe opsonization by both the classical and alternate pathways.

The opsonic ability of immunoglobulin is determined from the amount or number of infectious agents remaining after incubation. In a cell-mediated bactericidal assay, this is accomplished by comparing the number of surviving bacteria between two similar assays, only one of which contains the purported opsonizing immunoglobulin. Alternatively, the opsonic ability is determined by measuring the numbers of viable organisms before and after incubation. A reduced number of bacteria after incubation in the presence of immunoglobulin indicates a positive opsonizing ability. In the cell-mediated bactericidal assay, positive opsonization is determined by culturing the incubation mixture under appropriate bacterial growth conditions. Any significant reduction in the number of viable bacteria comparing pre- and post-incubation samples, or between samples which contain immunoglobulin and those that do not, is a positive reaction.

Clearance/Protective Assays

Another preferred method of identifying agents for the treatment or prevention of a staphylococcal infection employs a lethal model of *staphylococcus* sepsis that measures clearance and protection. Such agents can be immunoglobulin or other antimicrobial substances. This model can also be used for screening anti-Staphylococcal drugs.

A particularly useful animal model comprises administering an antibody, an immune suppressant, and a staphylococcal organism to an immature animal, followed by evaluating whether the antibody reduces mortality of the animal or enhances clearance of the staphylococcal organism from the animal. This assay may use any immature animal, including the rabbit, the guinea pig, the mouse, the rat, or any other suitable laboratory animal. The suckling rat lethal animal model, comprising an immature animal further immunosuppressed by the administration of an immune suppressant, is most preferred.

An immune suppressant is any substance which impairs the immune system of the animal to which it is administered, and is selected from the group consisting of steroids, anti-inflammatory agents, prostaglandins, cellular immune suppressants, iron, silica, particles, beads, lipid emulsions, and any other effective immune suppressant. Preferably, the immune suppressant is cyclosporin, dexamethasone, triamcinolone, cortisone, prednisone, ibuprofen, or any other related compound or combination of compounds. More preferably, the immune suppressant is a lipid emulsion, and the lipid emulsion of choice is intralipid. When the pharmaceutical composition is immunoglobulin, the assay measures the clearance potential of the administered immunoglobulin.

Clearance is evaluated by determining whether the pharmaceutical composition enhances clearance of the infectious agent from the animal. This is typically determined from a sample of biological fluid, such as blood, peritoneal fluid, or cerebrospinal fluid. The infectious agent is cultured from the biological fluid in a manner suitable for growth or identification of the surviving infectious agent. From samples of fluid taken over a period of time after treatment, one skilled in the art can determine the effect of the pharmaceutical composition on the ability of the animal to clear the infectious agent. Further data may be obtained by measuring over a period of time, preferably a period of days, survival of animals to which the pharmaceutical composition is administered. Typically, both sets of data are utilized. Results are considered positive if the pharmaceutical composition enhances clearance or decreases mortality. In situations in which there is enhanced organism clearance, but the test animals still perish, a positive result is still indicated.

Method of Isolating the Immunoglobulin

Still another embodiment of the present invention is isolated immunoglobulin. The assay may be any type of immunological assay, such as a binding assay, opsonization assay, or clearance assay as set forth above. The staphylococcal organism is preferably *S. epidermidis, S. hominus, S. simulans, S. haemolyticus*, a different coagulase negative staphylococcus species, or *S. aureus*. More preferably, the staphylococcal organism is *S. epidermidis* Serotype II. It is most preferred that the staphylococcal organism is Serotype II *S. epidermidis* Hay (ATCC 55133). Preferred staphylococcal organism preparations were described above.

Isolated immunoglobulin can be obtained from pooled or single units of blood, plasma, sera, or tissue, such as placenta, or from any immunoglobulin preparation derived therefrom, such as intravenous immunoglobulin (IVIG). Procedures for the isolation of immunoglobulin are well-known to those of ordinary skill in the art. Exemplary procedures are described in *Protein Purification: Principles and Practice* (R. K. Scopes, Springer-Verlag, New York, 1987), incorporated by reference.

Isolated immunoglobulin, including polyclonal antibodies, monoclonal antibodies, or a mixture thereof, can be one or more antibodies of any isotype, including IgG, IgM, IgD, IgA, or IgE, but is preferably IgG. Procedures for the identification and isolation of a particular fraction or isotype of antibody are well-known in the art. Exemplary methods are taught in *Current Protocols in Immunology* (Coligan et al., eds., John Wiley & Sons, New York, 1991), incorporated by reference. The present invention also includes methods for making these antibodies.

Methods for making polyclonal and monoclonal antibodies are known in the art. Certain methods, by way of example, are described in *Antibodies: A Laboratory Manual* (E. Harlow and D. Lane, Cold Spring Harbor Lab., 1988), incorporated by reference.

The present invention also encompasses the DNA sequence of the gene coding for the isolated monoclonal antibody. The DNA sequence can be identified, isolated, cloned, and transferred to a prokaryotic or eukaryotic cell for expression by procedures well-known in the art. For example, procedures are generally described in *Current Protocols in Molecular Biology* (Ausubel et al., eds., John Wiley & Sons, 1989), incorporated by reference.

Monoclonal IgG antibodies are preferable. IgG isotype antibodies can be made by isolating an IgG-producing hybridoma cell or by genetic manipulation. Also preferred is a method of producing purely or partly human monoclonal antibodies. Nonhuman or partly human antibodies may be made more human by chimerization or genetic manipulation.

The present invention includes an antigen binding site attached to the structural portion of an antibody molecule, or attached to another protein reactive in an assay with a preparation of a staphylococcal organism having broadly reactive surface antigens.

Isolated Antigen

Another embodiment of the present invention is isolated antigen, which is any single antigen, any mixture of different antigens, or any combination of antigens separated from an organism that elicits either of the immunoglobulins of the invention. Isolated antigen may comprise proteins, polysaccharides, lipids, glycoproteins, or any other suitably antigenic materials, but preferably comprises proteins, polysaccharides, and glycoproteins. Most preferably, isolated antigen contains proteins and glycoproteins. Isolated antigen can also be a single purified antigen or a small number of purified antigens, such as proteins, polysaccharides, glycoproteins, or synthetic molecules.

In a preferred embodiment, the isolated antigen is the 45–50 Kd surface protein of *S. epidermidis*. Although any organism bearing the antigens that induce the broadly reactive antibodies of the invention can be the source of the isolated antigen, a preferred source is Serotype II *S. epidermidis* Hay (ATCC 55133). In another preferred embodiment, the isolated antigen is from the capsular polysaccharide of a Serotype II *S. epidermidis* although, again, any organism bearing the antigens that induce the virulence marking antibodies of Serotype II *S. epidermidis* Hay (ATCC 55133) is preferred.

Methods of macromolecular purification include filtration, fractionation, precipitation, chromatography, affinity chromatography, HPLC, FPLC, electrophoresis, and any other suitable separation technique. Methods for the purification of proteins are well-known in the art.

The antigens may be purified, substantially purified, or partially purified. Exemplary protein purification methods are described in *Proteins: Structures and Molecular Properties* (T. E. Creighton, W.H. Freeman and Co., New York, 1984); and *Carbohydrate Analysis: A Practical Approach, 2nd Edition* (D. Rickwood, ed., IRL Press, Oxford England, 1984), incorporated by reference. Exemplary methods for the identification, production, and use of synthetic antigens are described in *Laboratory Techniques in Biochemistry and Molecular Biology: Synthetic Polypeptides as Antigens* (R. H. Burden and P. H. Knippenberg, eds., Elsevier, New York, 1988), incorporated by reference.

The present invention also encompasses recombinant antigens. The DNA sequence of the gene coding for the isolated antigen can be identified, isolated, cloned, and transferred to a prokaryotic or eukaryotic cell for expression by procedures well-known in the art. For example, procedures are generally described in *Current Protocols in Molecular Biology* (Ausubel et al., eds., John Wiley & Sons, 1989), incorporated by reference.

Upon introduction into a host, isolated antigen generates a polyclonal or monoclonal antibody broadly reactive and opsonic in an assay with a staphylococcal organism preparation. Preferably, the staphylococcal organism is Serotype II *S. epidermidis* Hay (ATCC 55133).

Pharmaceutical Compositions

The present invention also discloses a pharmaceutical composition comprising isolated immunoglobulin, including polyclonal and monoclonal antibodies, and a pharmaceutically acceptable carrier. The pharmaceutical compositions of the invention may alternatively comprise isolated antigen and a pharmaceutically acceptable carrier.

Pharmaceutically acceptable carriers can be sterile liquids, such as water, oils, including petroleum oil, animal oil, vegetable oil, peanut oil, soybean oil, mineral oil, sesame oil, and the like. With intravenous administration, water is a preferred carrier. Saline solutions, aqueous dextrose, and glycerol solutions can also be employed as liquid carriers, particularly for injectable solutions. Suitable pharmaceutical carriers are described in *Remington's Pharmaceutical Sciences*, 18*th Edition* (A. Gennaro, ed., Mack Pub., Easton, Pa., 1990), incorporated by reference.

Methods of Treatment with Immunoglobulin

Additionally, the invention teaches a method for treating a patient infected with, or suspected of being infected with, a staphylococcal organism. The method comprises administering a therapeutically effective amount of a pharmaceutical composition comprising immunoglobulin (either polyclonal or monoclonal antibodies) and a pharmaceutically acceptable carrier. A patient can be a human or other animal, such as a dog, cat, cow, sheep, pig, or goat. The patient is preferably a human.

A therapeutically acceptable amount of immunoglobulin is an amount reasonably believed to provide some measure of relief or assistance in the treatment or prevention of a staphylococcal infection. Such therapy may be primary or supplemental to additional treatment, such as antibiotic therapy, for a staphylococcal infection, an infection caused by a different agent, or an unrelated disease.

A further embodiment of the present invention is a method of preventing staphylococcal infection, comprising administering a prophylactically effective amount of a pharmaceutical composition or a passive vaccine, comprising immunoglobulin, polyclonal or monoclonal antibodies, and a pharmaceutically acceptable carrier. Treatment comprises administering the pharmaceutical composition by intravenous, intraperitoneal, intracorporeal injection, intra-articular, intraventricular, intrathecal, intramuscular, subcutaneous, intranasally, intravaginally, orally, or by any other effective method of administration of a prophylactically effective amount. The composition may also be given locally, such as by injection to the particular area infected, either intramuscularly or subcutaneously. Administration can comprise administering a prophylactically effective amount of immunoglobulin by swabbing, immersing, soaking, or wiping directly to a patient. The treatment can also be applied to objects to be placed within a patient, such as dwelling catheters, cardiac values, cerebrospinal fluid shunts, joint prostheses, other implants into the body, or any other objects, instruments, or appliances at risk of becoming infected with *staphylococcus*, or at risk of introducing a staphylococcal infection into a patient.

Method of Treatment with Isolated Antigen

Another preferred embodiment of the present invention is a vaccine comprising isolated antigen and a pharmaceutically acceptable carrier. Upon introduction into a host, the vaccine generates an antibody broadly protective and opsonic against staphylococcal infection. Isolated antigen can be any single antigen, any mixture of different antigens, or any combination of antigens.

Vaccinations are particularly beneficial for individuals known to be or suspected of being at risk of staphylococcal infection. This includes patients receiving body implants, such as valves, patients with indwelling catheters, patients preparing to undergo surgery involving breakage or damage of skin or mucosal tissue, certain health care workers, and patients expected to develop impaired immune systems from some form of therapy, such as chemotherapy or radiation therapy.

Method of Evaluating Efficacy

A still further embodiment of the present invention is a method for evaluating the efficacy of a pharmaceutical composition useful for treating an infectious agent, comprising administering a pharmaceutical composition, an immune suppressant, and an infectious agent to an immature animal, preferably an immune suppressed suckling rat. This is followed by evaluating whether the pharmaceutical composition reduces mortality of the animal or enhances clearance of the infectious agent from the animal. This method can be used where the infectious agent is a bacterium, preferably a gram positive bacterium, a parasite, a fungus, or a virus.

Immune suppressants are described above. The pharmaceutical composition is administered prophylactically for evaluating the efficacy of the pharmaceutical composition in enhancing resistance to an infectious agent or therapeutically for evaluating the efficacy of the pharmaceutical composition comprising the broadly reactive and opsonic immunoglobulin or antimicrobial agent in directly killing the infectious agent or enhancing the immune response of a multiply immunocompromised and lethally infected animal to fight off the infection.

Diagnostic Kit

A still further embodiment of the present invention is a diagnostic kit and aid for detecting a staphylococcal infection. The diagnostic aid comprises broadly reactive immunoglobulin (such as polyclonal or monoclonal antibodies) or isolated broadly reactive antigen, and a sample of biological fluid containing or suspected of containing antigen or antibody to *staphylococcus*.

A method for detecting staphylococcal infection in an animal comprises adding a biological sample containing or suspected of containing antibody specific for *staphylococcus* to isolated antigen, followed by determining the amount of binding between the antibody and the antigen. Alternatively, this method comprises adding a biological sample comprising or suspected of comprising *staphylococcus* antigen to immunoglobulin specific for a preparation of a staphylococcal organism, followed by determining the amount of binding between antigen present in the sample and the immunoglobulin. The immunoglobulin can be polyclonal or monoclonal antibody, but is preferably monoclonal antibody.

Exemplary methods are taught in *Immunology: A Synthesis* (E. S. Golub, Sinauer Assocs., Inc., Sunderland, Ma., 1987), incorporated by reference.

In one example, the diagnostic aid can be used to identify in a laboratory isolate human pathogenic *staphylococcus*. Staphylococci can be grouped into two groups based on a coagulase test: coagulase-negative, of which *S. epidermidis* is the most common pathogen, and coagulase-positive, of which *S. aureus* is the most common pathogen. Most, if not all, human pathogenic *S. epidermidis* are Serotype II coagulase-negative. Preliminary data shows that human pathogenic staphylococci react with antisera to the Serotype II capsular polysaccharide of *S. epidermidis*. Thus, the Serotype II capsular antigen appears to be a human virulence marker.

A laboratory isolate can be any organism isolated by microbiological techniques from, for example, a human source, an animal source, or other source. Laboratory isolates may also contain nonpathogenic contaminants.

The diagnostic aid is useful or determining if staphylococci, particularly coagulase-negative Serotype II staphylococci, present in the isolate are pathogenic for humans. The methods described above for performing assays are applicable in this embodiment.

Another use of the diagnostic aid is for identifying staphylococci and antigens thereof in body fluids of an animal. For example, a diagnostic aid reactive with coagulase-negative pathogenic staphylococci can be used to identify the presence of pathogenic staphylococci or antigens thereof in body fluids. Body fluids that can be tested include, but are not limited to, cerebrospinal fluid, blood, peritoneal fluid, and urine. The diagnostic aid is employed according to the methods described above. Detection using this diagnostic aid can be performed in cases of actual, suspected, acute, or chronic infection with staphylococci. Likewise, antigens from pathogenic staphylococcal organisms can be used to detect antibody to pathogenic organisms in blood and body fluids.

Method of Detecting a Pharmaceutical Composition

A further object of the present invention is a method for detecting a pharmaceutical composition in a biological sample. When a pharmaceutical composition comprises immunoglobulin, the method comprises adding a biological sample containing the pharmaceutical composition to isolated antigen, followed by determining the amount of binding between the pharmaceutical composition and the isolated antigen. Alternatively, when the pharmaceutical composition comprises isolated antigen, this method comprises adding a biological sample comprising the pharmaceutical composition to an antibody specific for the pharmaceutical composition, followed by determining the amount of binding between the pharmaceutical composition and the antibody.

These methods may be used, inter alia, to determine the pharmacokinetics of the pharmaceutical composition comprising broadly reactive and opsonic immunoglobulin. With this information, better care can be provided by determining the best dosage regimen and course of treatment with a pharmaceutical composition.

The following examples set forth the various aspects of the invention.

EXAMPLE 1

The purpose of this example is to demonstrate that large immunoglobulin pools can not ensure the presence of a high titer of antibody to *S. epidermidis*.

IgG fractions of standard intravenous immunoglobulin (IVIG) were used in experiments to represent large immunoglobulin pools. Preparations of various pools of IgG from several companies were analyzed for comparison (Gamimmune, Cutter Labs., Inc., Berkeley, Calif.: Sandoglobuin, Sandoz, East Hanover, N. J.; Gammagard, Hyland, Los Angeles, Calif.; Polygam, American Red Cross, Washington, D.C.).

Samples from each of these pools, and one sample from an individual patient (SAM), were tested for binding in an enzyme-linked immunosorbent assay (ELISA) against a preparation of *S. epidermidis*. Although any *S. epidermidis* strain can be used, the experiments used Hay, a clinical strain isolated from the blood of a child with *S. epidermidis* sepsis. This strain is on deposit at the American Type Culture Collection (ATCC) under Accession No. 55133.

Briefly, a culture of *S. epidermidis* (Hay, ATCC 55133) was grown to log phase (18–36 hours) at 37° C. in 1600 ml aliquots of tryptic soy broth (Difco Labs., Detroit, Mich.). The culture was centrifuged at 5000 rpm for 10 minutes and the cell buttons resuspended in a small volume (10–25 mls) of 2% TCA at pH 2.0. The TCA suspensions were combined and stirred overnight at 4° C., and the next day, the combined suspension was centrifuged at 5000 rpm for 10 minutes, the supernatants aspirated and saved, and the cell buttons discarded. Supernatants were combined with four volumes of absolute ethanol and stored overnight at 4° C. This solution was centrifuged at 2500 rpm for 10 minutes, the supernatants aspirated and discarded, and the antigen precipitates resuspended in saline and cultured to ensure sterility. Saline suspensions were lyophilized and stored at 4° C.

TCA-extracted antigen for ELISA testing was made from each serotype by dissolving 1.0 mg of lyophilized extract in 40 mls of coating buffer. Coating buffer was prepared by combining 1.59 g $Na_2CO_3$, 2.93 g $NaHCO_3$, and 0.2 g $NaN_3$ and adding distilled water to a final volume of 1000 mls. This solution was adjusted to a pH of 9.6. One hundred microliter aliquots of the antigen-containing solution were added to each well of 96-well microtiter plates, using separate plates for each serotype. Plates were incubated overnight at 4° C., after which wells were emptied and rinsed four times with PBS-Tween. PBS-Tween was prepared by combining 8.0 g NaCl, 0.2 g $KH_2PO_4$, 2.9 g $Na_2HPO_4$, 0.2 g KCl, 0.2 g $NaN_3$, and 0.5 mls of Tween-20, and adding distilled water to a final volume of 1000 mls. The solution was adjusted to a pH of 7.4. Samples of 100 µls from each pool of immunoglobulin were added to wells. Plates containing antisera were incubated at 4° C. for two hours, after which the plates were again emptied and rinsed four times with PBS-Tween. A 1/400 dilution of stock alkaline phosphatase-conjugated goat anti-rabbit IgG (Sigma Chem. Co., St. Louis, Mo.) was prepared in PBS-Tween. Aliquots of 40 µls were added to each well of the microtiter plates and the plates were incubated for two hours at 4° C. The plates were again emptied and rinsed four times with PBS-Tween. A 1 mg/ml solution of p-nitrophenyl phosphate (Sigma Chem. Co., St. Louis, Mo.) was prepared in diethanolamine buffer and 100 µl aliquots of this solution were added to each well of the microtiter plates. Diethanolamine buffer was prepared by combining 97 mls diethanolamine and 0.2 g $NaN_3$, and adding distilled water to a final volume of 1000 mls. The solution was adjusted to a pH of 9.8. The plates were incubated at 37° C. for two hours. Absorbance was measured at 405 nm using the Multiskan® MCC/340 instrument (Flow Labs., Lugano, Switzerland).

TABLE I

Antigen Binding Activity of Human Immunoglobulin for *Staphylococcus epidermidis* (ATCC 55133)

| Immunoglobulin; Source | Lot | Optical Density |
|---|---|---|
| Baxter | 609 | 0.707 |
| Baxter | 224 | 0.648 |
| Sandoz | 163 | 0.731 |
| Sandoz | 110 | 0.786 |
| Sandoz | 069 | 0.901 |
| Cutter | 40P07 | 1.014 |
| Cutter | 2801 | 0.666 |
| Cutter | 40R09 | 1.026 |
|  | SAM | 1.002 |

As indicated in Table I, there was a marked difference in the binding activity of each pool tested. Most samples contained low levels of antibody to *S. epidermidis*. Interestingly, a sample with one of the lowest activities (2801) and the sample with the highest (40R09) are from the same source, Cutter Laboratories. Among the higher binding pools, 069 and 40R09 were obtained from separate companies.

This data indicates that no single method of immunoglobulin preparation, i.e., unscreened plasma or IgG pool, can ensure the presence of a high titer of antibody to *S. epidermidis*, despite the fact that each of the tested pools represent very large collections of human sera. Variations in the content of reactive antibody occurred between preparations prepared by the same company and between lots of the same preparation, indicating that all immunoglobulin pools are distinct and that differences in the content of a specific-identifiable antibody can be striking.

EXAMPLE 2

In a second immunoglobulin binding study, random samples of plasma from almost one hundred human patients were screened in an ELISA. Antibody titers to four different strains of *S. epidermidis* were determined. One strain was obtained from the American Type Culture Collection, Rockville, Md. (ATCC 31423; Serotype 1). Two others, Serotypes 2 and 3, were provided by Dr. Y. Ichiman of the St. Marianna University School of Medicine, Japan, described in Y. Ichiman, *J. Appl. Bacteriol.*, 56:311 (1984).

Preparations of each strain were prepared as before. The ELISA was performed as previously described, except that 40 μls of each sample were used. As shown in FIG. 1, a significant number of samples contained antibody to each strain of *S. epidermidis*, including the clinical strain, Hay (ATCC 55133).

This data indicates that although there was a great deal of variability in binding, cross-reacting antibodies may be present within a single sample.

EXAMPLE 3

Pooled immunoglobulin could contain antibodies against a variety of *S. epidermidis* strains, which would mimic a single broadly reactive antibody. Therefore, studies were performed by immunizing animals with a single *S. epidermidis* strain to determine if exposure to this single strain would induce broadly reactive antibody.

Rabbits were immunized with either a heat-killed whole cell or TCA-extracted antigens of *S. epidermidis*. TCA-extracted antigens of *S. epidermidis* were prepared as described. One milligram of this preparation was dissolved in 1.0 ml of normal saline, and administered intramuscularly to New Zealand White rabbits. Following a one week rest, a second 1.0 ml dose was given. A final dose given one week later completed the primary immunization series. An identical third (P3), fourth (P4), or fifth (P5) course of immunization can be included, and additional booster series can be used to further elevate specific antibody levels. Further booster immunizations were given at additional intervals.

The bacterial whole cell vaccine was prepared as follows. Tryptic soy broth was inoculated with *S. epidermidis* (Hay, ATCC 55133) and incubated for three hours at 37° C. A 20 ml aliquot of this preparation was centrifuged at 3000 rpm for 10 minutes, the supernatant discarded, and the cell pellet resuspended in normal saline. A second washing with saline was carried out following a repeat centrifugation. The final suspension was prepared in saline to yield a total volume of 10 mls. The bacteria were heated to 56° C. for 60 minutes to produce the heat killed whole cell vaccine, which was cultured to ensure sterility.

One milliliter of this whole cell preparation was administered intravenously to New Zealand White rabbits daily for five days. After a one week rest, the rabbits were again immunized daily for five days. An identical third (P3), fourth (P4), or fifth (PS) course of immunization can be included, and additional booster series can be used to further elevate specific antibody levels. Further booster immunizations were given at additional intervals.

Sera obtained after immunization with the whole cell preparation showed a marked increase in antibodies to *S. epidermidis*, while the overall magnitude of the immune response was reduced in serum obtained after TCA-extracted antigen immunization (FIGS. 2 and 3). Sera induced by animals immunized with TCA-extracted antigens or whole cell vaccine produced broadly reactive antibodies to Serotypes I, II, and III of *S. epidermidis* plus the vaccine strain, *S. epidermidis* Hay (ATCC 55133), as determined by ELISA. Moreover these postimmunization antisera were broadly opsonic. (FIGS. 6 and 7).

As the animals were exposed only to a single strain, and as there was an equivalent background level of binding before immunization, it is clear that both preparations of *S. epidermidis* produced antibodies reactive with multiple *S. epidermidis* serotypes.

The lethal, neonatal *S. epidermidis* sepsis model shows that opsonic antibodies enhance clearance of bacteria from the blood and improve survival. Thus, consistent with the findings of K. Yoshida and Y. Ichiman, antibodies to Serotype II *S. epidermidis* capsule are protective against Serotype II polysaccharide-bearing bacteria. The results in the lethal sepsis model show that protection is mediated through opsonic antibodies that enhance bacterial clearance from the blood.

EXAMPLE 4

All antibodies, even those directed against a given organism, may not enhance immunity and provide enhanced protection from infection. Stated differently, antibodies which bind an antigen may not necessarily enhance opsonization or clearance of the organism from the infected animal and enhance survival. Therefore, a neutrophil mediated bactericidal assay was used to determine the functional activity of antibody to *S. epidermidis*.

Neutrophils were isolated from adult venous blood by dextran sedimentation and Ficoll-Hypaque® density centrifugation. Utilizing a microtiter plate assay requiring a total volume of 0.1 ml/well, washed neutrophils (approximately $10^6$ cells) were added to round-bottomed microtiter wells, along with approximately $3 \times 10^4$ mid-log phase bacteria (*S. epidermidis* Hay, ATCC 55133). Newborn rabbit serum (10 μls), screened to assure absence of antibody to *S. epidermidis*, served as a source of active complement. Forty microliters of 5% standard IVIG (or serum) were added at various dilutions, and the microplates were incubated at 37° C. with constant, vigorous shaking. Samples of 10 μls were taken from each well at zero time and after 2 hours of incubation, diluted, vigorously vortexed to disperse the bacteria, and cultured on blood agar plates overnight at 37° C. to quantitate the number of viable bacterial colonies. Controls consisted of neutrophils plus complement alone, and neutrophils plus complement. The opsonic activity determined as percent bacterial killing is calculated using the formula ([number bacteria (zero time−2 hours)]/[number bacteria at zero time])×100.

TABLE IIa

Opsonic Activity for Pools of Human Immunoglobulin for *Staphylococcus epidermidis*

| Immunoglobulin | Opsonic Activity (Percent) |
|---|---|
| Cutter | |
| 801 | 45 |
| 926 | 0 |

TABLE IIa-continued

Opsonic Activity for Pools of Human Immunoglobulin for Staphylococcus epidermidis

| Immunoglobulin | Opsonic Activity (Percent) |
|---|---|
| P07 | 92 |
| R09 | 90 |
| Sandoz | |
| 100 | 3 |
| 163 | 8 |
| 110 | 12 |
| 069 | 15 |
| Baxter | |
| 807 | 23 |
| 609 | 18 |
| 224 | 54 |
| 004 | 54 |
| SAM | 97 |
| control* | 0 |

(*= neutrophil plus complement alone)

Opsonic activity varied from 0% to 23% and from 90% to 97% in the samples. As was observed in the binding assay, no correlation could be drawn between preparative techniques used and functional activity observed. However, some of the immunoglobulin having a high degree of binding in Table I (O.D. >1.0), also had a high level of opsonic activity in Table IIa (e.g., 40P07, 40R09 and SAM).

Opsonophagocytic bactericidal activity of a 90% (>1 log reduction in bacteria over 2 hours) was arbitrarily chosen to indicate high opsonic activity.

TABLE IIb

Opsonophagocytic Bactericidal Activity of Pools of Human Immunoglobulin (IVIG) Preparations for 3 Staphylococcus epidermidis Strains

| Immunoglobulin | Opsonophagocytic Bactericidal Activity | | |
|---|---|---|---|
| Source Lot | Strain 31432 | Strain 35984 | Strain 55133 |
| Cutter | | | |
| 801 | 45% | 59% | 49% |
| 926 | 0 | 66% | 58% |
| P07 | 92% | 88% | 92% |
| R09 | 90% | 89% | 79% |
| Sandoz | | | |
| 100 | 3% | 0 | 0 |
| 163 | 8% | 0 | 0 |
| 110 | 12% | 8% | 0 |
| 069 | 15% | 23% | 43% |
| Baxter | | | |
| 807 | 23% | 62% | 48% |
| 609 | 18% | 62% | 48% |
| 224 | 54% | 53% | 0 |

(*IVIG was tested at a final concentration of 20 mg/ml IgG.)

These results show that only some of the immunoglobulin that bound to TCA-extracted antigens of S. epidermidis promoted phagocytosis and killing of S. epidermidis. Thus, for the first time using in vitro screening assays, it is possible to select immunoglobulin having high levels of antibody for S. epidermidis and having reliable levels of antibody to prevent and treat S. epidermidis infections.

EXAMPLE 5

It was important to determine if the opsonic antibodies for S. epidermidis were specifically directed against serotype specific S. epidermidis antigens or if the opsonic antibodies were directed against common staphylococcal antigens. To investigate these alternatives, selected high-titer immunoglobulin was preabsorbed with a preparation of S. epidermidis Hay (ATCC 55133) and tested for opsonic activity against three different gram positive cocci.

Absorbing bacteria were grown overnight on blood agar plates, scraped from the plates, suspended in normal saline, and pelleted in 0.5 ml microfuge tubes to one-fifth the volume of the tube. After adding 0.4 mls of immunoglobulin to each, the tubes were vortexed and rotated at a slow speed on an end-over-end tumbler (Fisher Scientific Co., Pittsburgh, Pa.) at 4° C. overnight. Bacteria were sedimented the following day in a microfuge tube and the supernatant was removed and filtered through a 0.2 µm membrane filter. The sterile immunoglobulin, containing no detectable S. epidermidis binding antibodies, was used either directly or after storage at 70° C.

Selected high-titer immunoglobulin (directed immunoglobulin) showed opsonization of the two species of staphylococcus, S. epidermidis and S. aureus, and the one species of Streptococcus tested, S. agalactiae (FIG. 4). With selected immunoglobulin preabsorbed with a preparation of S. epidermidis, opsonic activity to S. epidermidis was completely removed (95% to 0% bactericidal activity). However, opsonic activity against Streptococcus agalactiae, a different genus, was not diminished (93% to 94%). Surprisingly, a reduction in opsonic activity was observed for S. aureus (kindly provided by Dr. Mendiola of the Walter Reed Army Medical Center), present in the selected immunoglobulin at about half the level as antibody activity to S. epidermidis.

The results also suggest the existence of antibodies to antigens shared by S. epidermidis and S. aureus. Therefore, this selected immunoglobulin preparation promoted opsonization by common anti-staphylococcal antibodies that can be identified by absorption with S. epidermidis.

In the absence of antibody, there was no bactericidal activity demonstrated against any of the bacteria (neutrophil plus complement alone). These results indicate that the anti-staphylococcal antibodies are directed against key staphylococcal antigens that provide both specific protection against S. epidermidis and broad protection against other staphylococcus serotypes and species.

EXAMPLE 6

Opsonic activity was determined for serum from rabbits immunized with TCA-extracted antigens of S. epidermidis and a whole cell preparation of S. epidermidis.

Rabbits were immunized with either TCA-extracted antigens or whole cell preparation of S. epidermidis Hay (ATCC 55133). Sera was collected as before and tested for opsonizing activity against Serotype I, II, and III strains of S. epidermidis, and S. epidermidis Hay (ATCC 55133) in the neutrophil mediated bactericidal assay. As shown in FIGS. 5 and 6, both TCA-extracted antigens and whole cell preparations induced an antibody response with very high opsonic activity against all three serotypes. Although pre-vaccinated serum using the TCA-extracted antigens did show some activity against Serotype I (FIG. 5), opsonizing activity nearly doubled after inoculation, indicating that staphylococcal common antibodies were indeed responsible.

These data show that antibodies to *S. epidermidis* capsular antigens are important for immunity, and that one or more antigens may be antigenically similar between different serotypes.

EXAMPLE 7

The opsonizing activity of vaccinated rabbit sera was again determined using *S. aureus* Serotype 5 as the test bacterium (FIG. 7). Overall opsonizing activity against *S. aureus* was not as high as activities observed against strains of *S. epidermidis*, but serum samples from immunized animals did provide significant activity as compared to unvaccinated samples.

This data indicates that opsonizing antibodies to *S. epidermidis* are also protective against *S. aureus*, and again suggests that these antibodies may be directed against one or more staphylococcal common antigens.

EXAMPLE 8

Many bacteria, including *S. epidermidis*, are not pathogenic in normal humans. However, in infants with an immature immune system and in individuals with an impaired immune system, *S. epidermidis* can cause sepsis and even death. Therefore, in any animal model of sepsis it is critical to include these factors. By utilizing an animal with an immature immune system and subjecting the animal to immunological suppressant, sepsis in human patients can be studied.

To demonstrate that IVIG with opsonic antibody directed against *S. epidermidis* could provide protection from lethal *S. epidermidis* sepsis, a suckling rat lethal animal model was developed. Suckling rats infected with $5 \times 10^7$ *S. epidermidis* subcutaneously developed bacteremia within two hours, and cleared over 72 hours (Table III).

TABLE III

Induction of Bacteremia and Sepsis in Suckling Rats After Challenge with *Staphylococcus epidermidis* (ATCC 55133)

| Time Post Infection | Number Bacteremic* | Percent Bacteremic | Bacteria/Ml Blood (geometric mean) |
|---|---|---|---|
| 2 hours | 8/8 | 100 | $3.8 \times 10^2$ |
| 4 hours | 7/8 | 87.5 | $1.3 \times 10^2$ |
| 6 hours | 8/8 | 100 | $7.5 \times 10^2$ |
| 14 hours | 6/8 | 75 | $8.8 \times 10^1$ |
| 18 hours | 3/8 | 37.5 | $0.5 \times 10^1$ |
| 22 hours | 0/8 | 0 | 0 |

(*8/8 (100%) infected rat pups survived)

All of the animals cleared bacteremia within 72 hours after infection (Table III), suggesting that under normal circumstances, neonatal immunity, although impaired, can eventually control *S. epidermidis*. However, some studies in rats infected with *S. epidermidis* shortly after birth have demonstrated that a lethal infection can still develop (data not shown).

EXAMPLE 9

The effect of intralipid on *S. epidermidis* mortality in suckling rats was assayed. Wistar rats were injected with intralipid, an immune suppressant, just after birth. Animals were administered intralipid beginning on day two of life. Two doses were administered each day for two days. With the final dose of intralipid, animals were also given selected immunoglobulin or saline. After this final dose the animals were infected by subcutaneous injection with a preparation of *S. epidermidis* Hay (ATCC 55133). Blood samples were subcultured onto plates to ensure that bacteremia was caused by *staphylococcus* and to follow clearance after therapy. All animals were followed for five days to determine survival.

TABLE IV

Animal Model: The Effect of Intralipid Dose on *Staphylococcus epidermidis* Mortality in Suckling Rats

| Intralipid Dose* | Infected | | Survival Control | |
|---|---|---|---|---|
| 4 gm/kg | 10/10 | 100% | 7/7 | 100% |
| 8 gm/kg | 10/13 | 76% | 9/9 | 100% |
| 12 gm/kg | 7/12 | 58% | 11/11 | 100% |
| 16 gm/kg | 6/13 | 46% | 11/11 | 100% |
| *16 gm/kg | 2/6 | 33% | 5/5 | 100% |

*= Intralipid was given at a dose of 4 gm/kg (up to 4 doses over 2 days) IP with the final dose given on day 3 of life, approximately 30–60 minutes prior to infection with *S. epidermidis*.

Animals receiving only *S. epidermidis* successfully overcame infection and survived. Only those animals treated with intralipid prior to infection showed a marked decrease in their ability to resist *S. epidermidis*.

The administration of lipid emulsion simulates lipid administration commonly given to neonates, previously shown to impair bacterial clearance (Fischer et al., *Lancet*, 2:819 (1980)). In contrast to the results of Example 8, where all the pups survived treatment, at a dosage of >8 gm/kg prior to *S. epidermidis* challenge, survival decreased in direct proportion to the quantity of lipid administered.

Control animals given lipid emulsion without infection suffered no apparent effects. This model may be very relevant for newborn babies, since lipid emulsion therapy has previously been associated with *S. epidermidis* bacteremia in neonates (Freeman et al., *Eng. J. Med.*, 323:301–308 (1990)). For IVIG treatment studies, all animals received 16 gm/kg lipid emulsion before *S. epidermidis* challenge. All pups treated with IVIG containing ≧90% opsonic activity for *S. epidermidis* survived (FIG. 10). Those treated with absorbed IVIG had a mortality similar to those treated with saline placebo (Survival 11/11 [100%], 9/22 [41%], and 8/15 [53%], respectively; p<0.001 IVIG vs. Absorbed IVIG by Fisher's exact test).

EXAMPLE 10

The effectiveness of selected high-titer (directed) immunoglobulin in providing protection against a lethal infection of *S. epidermidis* Hay (ATCC 55133) was determined in the suckling rat lethal animal model.

Two day old Wistar rats were given two 0.2 ml intraperitoneal injections of 20% intralipid. The next day, animals were again given the same series of injections of 20% intralipid plus immunoglobulin or serum from vaccinated animals. After the last injection, approximately $5 \times 10^7$ cells of *S. epidermidis* Hay (ATCC 55133) were injected subcutaneously at the base of the tail. Mortality was determined for five days.

TABLE Va

Effectiveness of Immunoglobulin Directed Against *Staphylococcus epidermidis* in Providing Protection from Lethal Infection

| Immunoglobulin | Treated | Died | Mortality |
|---|---|---|---|
| Exp. #1 | | | |
| 40R09 | 24 | 0 | 0% |
| Standard Control | 20 | 4 | 20% |
| untreated | 13 | 7 | 54% |
| uninfected | 11 | 0 | 0% |
| Exp. #2 | | | |
| 40R09 | 13 | 2 | 8% |
| Vaccine Induced | 11 | 2 | 18% |
| Control - saline | 19 | 11 | 42% |

Directed immunoglobulin, selected for the ability to bind to or opsonize a preparation of *S. epidermidis* (lot No. 40R09), provided complete protection from lethal infection in an immune-impaired lethal animal model. These results are identical to the results obtained from uninfected animals. Unselected low-titer immunoglobulin (also called standard immunoglobulin) demonstrated 20% mortality, and other controls were as expected. Untreated and uninfected animals had greater than 50% mortality.

In a second, similar experiment, directed high-titer human immunoglobulin and vaccine induced high-titer rabbit serum, both strongly protective, produced nearly identical results. In contrast, a saline control had over 40% mortality.

Overall, these data suggest that antibodies directed against *S. epidermidis* are protective in the suckling rat lethal animal model.

EXAMPLE 11

Several IVIG lots from various suppliers were further analyzed to determine whether screening IVIG for *S. epidermidis*-specific opsonic antibody could identify IVIG that would consistently enhance protection (Table Vb). IVIG with >90% bactericidal opsonic activity against *S. epidermidis* was compared with IVIG lots with <50% opsonic activity for *S. epidermidis* or with saline. Survival was significantly increased in animals receiving IVIG with ≧90% opsonic activity when compared with animals receiving IVIG with <50% opsonic activity or saline.

TABLE Vb

Effect of IVIG on Survival in a Neonatal *Staphylococcus epidermidis* Sepsis Model

| Study Group | Animals Treated | Animals Survived | Percent Survival | Significance (Chi Square) |
|---|---|---|---|---|
| IVIG* (high titer) | 217 | 165 | 76% | p < 0.0001 |
| IVIG** (low titer) | 194 | 94 | 48% | p = 0.41 |
| Saline | 56 | 23 | 41% | |

*IVIG: 2 different products, with each lot having >90% opsonic activity for *S. epidermidis*.
**IVIG: 4 different products (5 lots), with each lot having <50% opsonic activity for *S. epidermidis*

A significant relationship (p=0.0034) was demonstrated by linear regression analysis between survival following infection with *S. epidermidis* and the *S. epidermidis* opsonic activity of the preparation administered (FIG. 12). Further studies were performed to determine if IVIG was protective against multiple *S. epidermidis* serotypes. An IVIG lot with ≧90% opsonic activity to *S. epidermidis* (clinical strain) provided enhanced survival in the neonatal suckling rat model for all serotype strains and the clinical isolate Hay (FIG. 9).

EXAMPLE 12

Immunoglobulin bound to a preparation of *S. epidermidis* in an ELISA assay, and opsonized *S. epidermidis* organisms in the cell mediated bactericidal assay (directed immunoglobulin), were tested for their capacity to promote clearance of *S. epidermidis* in the suckling rat model.

Blood samples were taken from infected animals at regular intervals (FIG. 8). Only directed immunoglobulin previously identified in an ELISA or opsonic assay decreased levels of bacteria over the course of treatment. These animals showed increased survival rates in Table Va. Immunoglobulin which did not opsonize or bind to a preparation of *S. epidermidis* did not promote clearance of bacteria from the blood of infected animals.

EXAMPLE 13

Antibody to *S. epidermidis* was analyzed in the suckling rat lethal animal model for the ability to enhance clearance and provide protection against an international geographically diverse group of *S. epidermidis* strains (FIG. 9).

Directed immunoglobulin enhanced survival was tested against *S. epidermidis* Hay (ATCC 55133, Serotype II), a prototype laboratory strain (ATCC 31432, Serotype I), and two distinct Japanese strains (Serotypes II and III). Directed immunoglobulin preabsorbed against a preparation of *S. epidermidis* showed no increase in survival (FIG. 10). Bacteria counts from blood samples taken during the study also showed that directed immunoglobulin rapidly cleared *staphylococcus* bacteremia. Rats treated with saline or preabsorbed immunoglobulin had persistent bacteremia and increased mortality (FIG. 11).

To determine if survival was related to functional anti-staphylococcus activity of antibody, immunoglobulin preparations with various levels of opsonophagocytic bactericidal activity for *S. epidermidis* (directed immunoglobulin) were compared with saline and preabsorbed immunoglobulin (which had no bactericidal activity for *S. epidermidis*).

A significant relationship was observed between opsonophagocytic bactericidal activity of antibody and survival in *staphylococcus* sepsis (FIG. 12). While saline, standard immunoglobulin, and preabsorbed directed immunoglobulin provided similarly poor protection (each had little or no opsonophagocytic bactericidal antibody), the unabsorbed directed immunoglobulin provided uniformly good survival. These results indicate that opsonic anti-staphylococcus antibodies are associated with survival.

EXAMPLE 14

Previous reports have suggested that there are multiple *S. epidermidis* serotypes. In addition, there are many other coagulase negative staphylococci besides *S. epidermidis*. For efficacious broadly reactive antibody, antibody ideally should cover human pathogenic coagulase negative staphylococci. Many coagulase negative staphylococci, however, rarely if ever cause infections in humans. Thus, it is important to determine if broadly reactive antibodies are capable of binding all human pathogenic coagulase negative bacteria.

Rabbits were immunized with staphylococci of one of three S. epidermidis strains (ATCC 31432, S. epidermidis 360, and S. epidermidis 10). S. epidermidis (ATCC 31432) is Serotype I, S. epidermidis 360 and S. epidermidis Hay (ATCC 55133) are Serotype II, and S. epidermidis 10 is Serotype III. The antisera were identified as follows: anti-I was raised against strain ATCC 31432; anti-II was raised against strain S. epidermidis 360; and anti-III was raised against strain S. epidermidis 10.

Coagulase negative staphylococci isolated from patients were speciated and characterized as pathogens if in a given patient there were >2 positive cultures from normally sterile sites (cultures obtained at different times or from different sites). These cultures were then reacted with rabbit antisera (anti-I, anti-II, and anti-III) in an ELISA assay.

ELISA Assay:

Preparation of ELISA plates: 100λ aliquots of S. epidermidis extracted antigens were added to wells of 96 well microassay plates (Nunclon®, Nunc, Denmark), and stored overnight at 4° C. Wells are gently washed with Tween (0.5 ml Tween 20/1 deionized $H_2O$) prior to use.

Preparation of antisera: Rabbit antisera anti-I, anti-II, and anti-III were produced according to the general method of Fischer et al., J. Exper. Med., 148:776–786 (1978). Antiserum preparations were then diluted 100 fold in PBS-Tween prior to use. Further serial dilutions were also carried out in PBS-Tween. The rabbit antisera (anti-I, anti-II, and anti-III) were prepared further by absorption with the two heterologous strains to remove common staphylococcal antibodies not specific to one of the strains.

Analysis of antibody reactivity: Microassay plates were prepared using 40λ of antisera at several dilutions (1/100 to 1/12800). Antisera was added to the appropriate wells of the microassay plate. Normal saline, used as a control, was similarly diluted. Plates were incubated at 4° C. for two hours. Alkaline phosphatase-conjugated goat anti-rabbit IgG (Sigma, St. Louis, Mo.) was prepared in a 1/400 dilution with PBS-Tween, and 40λ of this preparation was then added to each well in appropriate columns. To a single column of wells, only PBS-Tween was added. Plates were again incubated at 4° C. for two hours.

4-nitrophenyl phosphate was used as substrate for the enzymatic reaction, and was prepared by dissolving a 5 mg substrate tablet ($10^4$ phosphate substrate tablets, Sigma) in 5 ml of 10% diethanolamine buffer (see below). 100λ of this substrate preparation was then added to each well as appropriate after incubation at 37° C., and absorbance was then measured at 405 nm at 120 minutes using the Titertek® Multiskan MCC/340 instrument (Flow Laboratories, Lugano, Switzerland).

Preparation of reagents: Preparation of buffers from the methods of Voller et al, Bull. W.H.O., 53:55–64 (1976).

TABLE VI

| Preparation of Reagents | | | | | |
|---|---|---|---|---|---|
| Coating buffer (pH 9.6) | | PBS-Tween (pH 7.4) | | Diethanolamine buffer (pH 9.8) | |
| $Na_2CO_3$ | 1.59 g | NaCl | 8.0 g | Diethanol-amine | 97 ml |
| $NaHCO_3$ | 2.93 g | $KH_2PO_4$ | 0.2 g | $NaN_3$ | 0.2 g |

TABLE VI-continued

| Preparation of Reagents | | | | | |
|---|---|---|---|---|---|
| Coating buffer (pH 9.6) | | PBS-Tween (pH 7.4) | | Diethanolamine buffer (pH 9.8) | |
| $NaN_3$ | 0.2 g | $Na_2HPO_4$ | 2.9 g | $H_2O$ | to 1000 ml |
| $H_2O$ | 1000 ml | KCl | 0.2 g | | |
| | | Tween 20 | 0.5 ml | | |
| | | $NaN_3$ | 0.2 g | | |
| | | $H_2O$ | 1000 ml | | |

The results of these studies are shown in Table VII. Three coagulase negative staphylococci, in addition to S. epidermidis, were identified as human pathogens. Each of the pathogenic staphylococci reacted with rabbit antisera obtained after immunization with a single S. epidermidis strain, Serotype II S. epidermidis 360. Absorbing the antiserum from S. epidermidis 360 with the other two S. epidermidis strains (used to produce the other antisera but not this antisera) did not remove the staphylococcal-reactive antibodies induced by S. epidermidis 360.

Antisera raised against the other strains, however, did not react to any of the pathogenic strains after absorption with Serotype II S. epidermidis 360. In addition, Serotype II S. epidermidis Hay (ATCC 55133) reacted with the broadly reactive antisera, further showing that antigens from this organism bind antibodies in the broadly reactive antisera.

TABLE VII

Human Pathogenic* Coagulase Negative Staphylococci Reactive with Antibodies from Immunization with a Single Coagulase Negative Staphylococcus

| Organism | No. Isolated | Positive Reaction |
|---|---|---|
| S. epidermidis | 16 (57%) | 16/16 (100%) |
| S. haemolyticus | 8 (29%) | 8/8 (100%) |
| S. hominis | 3 (11%) | 3/3 (100%) |
| S. simulans | 1 (3%) | 1/1 (100%) |
| S. warneri | 0 | — |
| S. capitis | 0 | — |

*Isolates were selected only from patients with ≧2 positive cultures from sterile sites (different times or different sources).

Although S. epidermidis has been divided into 3 serotypes (Y. Ichiman and K. Yoshida, J. Appl. Bacteriol., 51:229 (1981)), it has not been shown that pathogenicity is associated with any specific strain or strains using mouse virulence testing (Y. Ichiman, J. Appl. Bacteriol., 56:311 (1984)). The results presented in this example demonstrate that all of the pathogenic human coagulase negative staphylococci reacted with antibodies elicited by immunization with a single Serotype II S. epidermidis strain.

The immunizing Serotype II S. epidermidis 360 strain and Serotype II S. epidermidis Hay (ATCC 55133) are both reactive with antisera to which all of the human pathogens reacted. The results demonstrate that antigens on the surface of the human pathogens, the immunizing S. epidermidis 360 and S. epidermidis Hay (ATCC 55133), are similar, and that the antigens are important virulence markers on many coagulase negative staphylococci, including S. epidermidis, S. hemolyticus, S. hominis, and S. simulans.

Antibodies to a single S. epidermidis strain with the proper constituents (such as S. epidermidis Hay (ATCC 55133)) can confer broad protection against coagulase negative staphylococci. Antibodies raised against these antigenic determinants are useful for distinguishing between pathogenic and nonpathogenic staphylococci in laboratory isolates. Such antibodies are also useful for detecting pathogenic staphylococci and antigens thereof, or antibodies directed against pathogenic staphylococci and antigens thereof, in mammalian body fluids such as cerebrospinal fluid, blood, peritoneal fluid, and urine.

In addition, the antigens that elicit these antibodies are useful for screening immunoglobulin for broadly opsonic and protective antibodies. The antigens are also useful for producing staphylococcal vaccines.

EXAMPLE 15

The present example determines the total protein composition of the various serotypes of S. epidermidis, and identifies proteins reactive with opsonic rabbit antisera.

Mouse antibody to capsular polysaccharide has been shown to be protective for homologous S. epidermidis serotypes, but not for heterologous serotypes (Yoshida et al., J. Appl. Bacteriol., 51:229 (1981)). Protection with human serum was also related to homologous, but not heterologous anti-capsular polysaccharide antibodies (Ichiman et al., J. Appl. Bacteriol., 63:165 (1987)). Although the mechanism of homologous protection was unclear, protection was thought to be mediated by IgM antitoxin.

The three serotypes of S. epidermidis, designated Serotype I, II, and III are based on the polysaccharide capsule of S. epidermidis. Rabbit immunization studies were conducted to determine if broadly protective antibodies to S. epidermidis were directed against multiple capsular polysaccharide serotype antigens, or against an antigen inducing broad protection across serotypes. After immunization with S. epidermidis Hay (ATCC 55133) inactivated whole cell vaccine (FIGS. 3 and 6), or TCA-extracted antigens, comprising surface proteins and polysaccharides (FIGS. 2 and 5), a rise in ELISA antibodies to TCA-extracted antigens from all serotypes was observed (FIGS. 2 and 3). In addition, opsonic antibodies were also induced by immunization with this single S. epidermidis strain (FIGS. 5 and 6).

Thus, the present invention surprisingly demonstrates that antibodies to S. epidermidis are broadly opsonic (FIGS. 5 and 6) and protective (FIG. 9) across all three serotypes. These data demonstrate that antibodies to non-polysaccharide capsular antigens are also opsonic and provide protection against infection by S. epidermidis.

These results suggest that a surface antigen of S. epidermidis Hay (ATCC 55133) induced broadly reactive opsonic antibodies across all three S. epidermidis serotypes. Such an antigen could account for the broad protection shown in the IVIG studies. Since polysaccharide capsular antigens induce serotype specific antibodies, the present example is directed to surface proteins of S. epidermidis.

To determine the total protein composition of the various serotypes of S. epidermidis, and to identify proteins reactive with opsonic rabbit antisera, samples of each serotype were analyzed by two-dimensional gel electrophoresis. One series of gels were silver stained to visualize the component proteins of each serotype. These gels were analyzed by image processing to compare both qualitative and quantitative expression of specific proteins (FIG. 13). Approximately 400 proteins could be resolved.

Another series of gels were transferred by electroblotting (Western transfer) to polyvinylidene difluoride membranes for analysis by immunodetection using the opsonic rabbit antisera to identify antigenic proteins.

Two-Dimensional Electrophoresis:

Current 2-D technology offers the highest resolution separations available and can resolve over two thousand different proteins from highly complex cells. This level of resolution, almost two orders of magnitude greater than competing techniques, makes this technique uniquely suited to the analysis of cellular protein components. The "maps" produced by this technology result in proteins appearing as a distinct oval or round spot when detected by staining.

The analysis of S. epidermidis proteins is based upon separation and characterization by two-dimensional gel electrophoresis using the ISO-DALT system of Anderson and Anderson. The 2-D system, with slight modifications, consists of isoelectric focusing in an acrylamide gel in the first dimension followed by slab gel electrophoresis in the second dimension. Isoelectric focusing separates proteins according to amino acid composition (primarily in relation to the ratio of acidic to basic chemical groups). Typically, a small sample of protein (100–200 µg) is applied to the top of a gel formed in a 1.5 mm glass tube, and separated over 20 hours at 700 V. Low molecular weight ampholytes added to the gel generate a pH gradient within the gel. The gel rod containing isoelectrically focused proteins is removed from the tube and placed along the top edge of an acrylamide slab gel containing sodium dodecyl sulfate, an anionic detergent that unfolds each protein. The proteins migrate under the influence of an applied electrical field and separate by a sieving action according to their molecular mass. Proteins focusing between pH 3 to 10 and within the molecular mass range of 8,000 to 250,000 daltons can be resolved. A two-dimensional array of spots, each composed of a specific protein, is formed. The protein spots are then detected by staining. Radiographic methods for detection may also be used if the proteins incorporate a radioactive label.

Identification and Purification of Proteins:

Proteins separated by two-dimensional gel electrophoresis are readily identified by immunological staining. The proteins are transferred from the acrylamide slab gel (generally prior to staining) by the method of Western blotting introduced by Towbin. This method uses a sandwich arrangement in which the proteins resolved in the acrylamide gel are electrophoretically transferred out of the gel matrix onto the surface of a membrane support, such as nitrocellulose or polyvinylidene difluoride. Proteins bound to the support can then be analyzed by immunochemical visualization reactions employing an antibody to a particular protein component. This is followed by a secondary antibody conjugated to an enzyme system, such as peroxidase or phosphatase, for visualization.

Using these techniques, one protein having a molecular weight of about 45–50,000 daltons was found to react strongly to the antisera. This protein, which focuses at a pH of approximately 4.5, is quantitatively one of the major proteins found in S. epidermidis. The protein was identified on all three S. epidermidis serotypes and in antigen preparations obtained by TCA extraction from these organisms. FIG. 13 shows the separation of this protein on a two-dimensional gel, indicated by the "X" on the large picture and on panel "D."

Since the reacting protein could be extracted from whole cell bacteria by TCA, it is most likely a S. epidermidis surface protein, important for phagocytosis and immunity. A S. epidermidis protein that induced broadly reactive and protective antibodies to all serotypes of S. epidermidis is valuable as a tool for screening plasma or immunoglobulins (polyclonal or monoclonal) useful for passive immunotherapy to prevent or treat *S. epidermidis* infections. In addition, this protein is useful for active immunization to induce protection against *S. epidermidis* by vaccination. Polyclonal serum containing opsonic antibodies against *S. epidermidis* bound to this protein, demonstrating that this is an important surface protein of *S. epidermidis* that may play a significant role in the prevention and treatment of staphylococcal infections.

Antibodies to this protein are therefore broadly protective against all serotypes of *S. epidermidis*, and are not serotype specific, as suggested by the studies of Y. Ichiman and K. Yoshida.

EXAMPLE 16

This example provides vaccines comprising Staphylococcal antigens useful for treating and preventing Staphylococcal infections.

Table VIII shows exemplary vaccines employing various types of antigens and target organisms. As noted in the Table, several of the vaccines are conjugate vaccines. Methods of conjugation are well known to those of ordinary skill in the art, and include the heteroligation techniques of Brunswick et al., *J. Immunol.*, 140:3364 (1988); Wong, S. S., *Chemistry of Protein Conjugates and Crosslinking*, CRC Press, Boston (1991); and Brenkeley et al., "Brief Survey of Methods for Preparing Protein Conjugates With Dyes, Haptens and Cross-Linking Agents," *Bioconjugate Chemistry*, 3, No. 1 (January 1992), specifically incorporated by reference.

Other conjugate vaccines could include antigens from gram-negative or gram-positive bacteria in a variety of combinations. For example, staphylococcal polysaccharides could be conjugated to proteins from gram-negative or gram-positive bacteria, or gram-negative or gram-positive bacterial polysaccharides could be conjugated to staphylococcal proteins.

This example is not intended to be limiting, and other types of vaccines will be apparent to those skilled in the art from consideration of the specification and practice of the invention.

TABLE VIII

| Vaccine | Type | Target Organisms |
|---|---|---|
| heat-killed S. epidermidis Hay (ATCC 55133) | whole cell | coagulase negative and positive A staphylococci |
| surface protein 45–50,000 Daltons | purified protein | S. epidermidis (all serotypes) |
| Serotype II polysaccharide | purified polysaccharide | human pathogenic staphylococci |
| surface protein conjugated to Serotype II S. epidermidis polysaccharide and Serotypes 5 and VIII S. aureus polysaccharide | conjugate vaccine | human pathogenic staphylococci |
| tetanus or diphtheria toxoid conjugated to Serotype II polysaccharide | conjugate vaccine | human pathogenic staphylococci |
| surface protein conjuaged to pseudomonas polysaccharide | conjugate vaccine | all serotypes of S. epidermidis and pseudomonas (gram positive and gram negative bacteria coverage) |

It is known that both protein and polysaccharide antigens on the surface of bacteria play an important role in immunity. As provided by this invention, the 45–50 Kd surface protein of one strain of *S. epidermidis* induces antibodies reactive against all three serotypes of *S. epidermidis*. This invention also demonstrates that the Serotype II *S. epidermidis* capsular polysaccharide is not only protective for Serotype II *S. epidermidis* (Ichiman et al., *J. Appl. Bacteriol.*, 63:165–169 (1987)), but is a common virulence marker for invasive coagulase negative staphylococci (Table VII), with all invasive strains bearing the Serotype II capsule. Thus, an organism that bears such antigens, such as Serotype II *S. epidermidis* Hay (ATCC 55133), is useful in isolating immunoglobulin that is both opsonic and broadly reactive (FIGS. 5 and 6) as well as indicating the presence of pathogenic staphylococci.

Such antigens are also useful in vaccines either alone, combined (i.e., a combination of the 45–50,000 dalton *S. epidermidis* surface protein and the Type II capsular polysaccharide), or combined with other important antigens. Such other antigens may include other staphylococcal capsular polysaccharides, such as Serotype 5 and Serotype 8 *S. aureus* capsular antigens, which are also important for inducing opsonic antibodies to staphylococci. Vaccines utilizing Serotype II polysaccharide alone are broadly reactive for coagulase negative staphylococci (CNS), but a vaccine combining Serotype II *S. epidermidis* and Serotypes 5 and 8 *S. aureus* polysaccharides would provide broadly reactive vaccine for staphylococci (coagulase negative and coagulase positive). Such vaccines would be highly immunogenic even in young infants and have broadly opsonic and protective activity for staphylococci.

To enhance immunogenicity, such polysaccharide antigens can be conjugated to proteins, such as tetanus or diphtheria toxoids, or staphylococcal proteins, as is well known in the art.

Other embodiments and uses of the invention will be apparent to those skilled in the art from consideration of the specification and practice of the invention. It is intended that the specification and examples be considered exemplary, with the true scope and spirit of the invention indicated by the following claims.

I claim:

1. Broadly reactive opsonophagocytic bactericidal immunoglobulin for treating a pathogenic coagulase-negative *Staphylococcus* infection, obtained by the process comprising:
    a) obtaining an immunoglobulin source chosen from at least one of serum, plasma, immunoglobulin pool, whole blood, and tissue or cells that produce or contain antibodies; and
    b) screening the immunoglobulin source to identify immunoglobulin that exhibits a high degree of binding to a TCA extract of serotype II *Staphylococcus epidermidis* by a high Optical Density of greater than 1 in an enzyme-linked immunosorbent assay (ELISA) which Optical Density has been correlated to an opsonophagocytic bactericidal activity of greater than or equal to 90% against a serotype II *Staphylococcus epidermidis*,
such that the identified immunoglobulin is broadly reactive against *Staphylococcus epidermidis* serotypes I, II, and III, exhibits a high degree of binding to a TCA extract of serotype II *Staphylococcus epidermidis* by a high Optical Density of greater than 1 in an ELISA, has opsonophagocytic bactericidal activity of greater than or equal to 90% against a serotype II *Staphylococcus epidermidis*, and is for treating a pathogenic coagulase-negative staphylococcal infection.

2. The broadly reactive opsonic immunoglobulin of claim 1, wherein the TCA extract of serotype II *Staphylococcus epidermidis* is derived from *Staphylococcus epidermidis* strain Hay (A.T.C.C. 55133).

3. The broadly reactive opsonic immunoglobulin of claim 1, wherein the opsonophagocytic bactericidal activity is determined by an in vitro complement-dependent neutrophil opsonization assay.

4. The broadly reactive opsonophagocytic bactericidal immunoglobulin of claim 1, wherein the tissue is a placenta.

5. The broadly reactive opsonophagocytic bactericidal immunoglobulin of claim 1, wherein the cells are hybridoma cells.

6. Broadly reactive opsonophagocytic bactericidal immunoglobulin for treating a pathogenic coagulase-negative *Staphylococcus* infection, obtained by the process comprising:
   a) obtaining an immunoglobulin source chosen from at least one of serum, plasma, immunoglobulin pool, whole blood, and tissue or cells that produce or contain antibodies;
   b) screening the immunoglobulin source to identify immunoglobulin that exhibits a high degree of binding to a TCA extract of serotype II *Staphylococcus epidermidis* by a high Optical Density of greater than 1 in an ELISA; and
   c) screening the immunoglobulin source of step b) to further identify immunoglobulin which has an opsonophagocytic bactericidal activity of greater than or equal to 90% against a serotype II *Staphylococcus epidermidis*, such that the identified immunoglobulin is broadly reactive against *Staphylococcus epidermidis* serotypes I, II, and III, exhibits a high degree of binding to a TCA extract of serotype II *Staphylococcus epidermidis* by a high Optical Density of greater than 1 in an ELISA, has opsonophagocytic bactericidal activity of greater than or equal to 90% against a serotype II *Staphylococcus epidermidis*, and is for treating a pathogenic coagulase-negative staphylococcal infection.

7. The broadly reactive opsonic immunoglobulin of claim 6, wherein the TCA extract of serotype II *Staphylococcus epidermidis* is derived from *Staphylococcus epidermidis* strain Hay (A.T.C.C. 55133).

8. The broadly reactive opsonic immunoglobulin of claim 6, wherein the opsonophagocytic bactericidal activity is determined by an in vitro complement-dependent neutrophil opsonization assay.

9. The broadly reactive opsonophagocytic bactericidal immunoglobulin of claim 6, wherein the tissue is a placenta.

10. The broadly reactive opsonophagocytic bactericidal immunoglobulin of claim 6, wherein the cells are hybridoma cells.

11. Broadly reactive opsonophagocytic bactericidal immunoglobulin for preventing bacteremia caused by a pathogenic coagulase-negative *Staphylococcus* infection, obtained by the process comprising:
   a) obtaining an immunoglobulin source chosen from at least one of serum, plasma, immunoglobulin pool, whole blood, and tissue or cells that produce or contain antibodies; and
   b) screening the immunoglobulin source to identify immunoglobulin that exhibits a high degree of binding to a TCA extract of serotype II *Staphylococcus epidermidis* by a high Optical Density of greater than 1 in an enzyme-linked immunosorbent assay (ELISA) which Optical Density has been correlated to an opsonophagocytic bactericidal activity of greater than or equal to 90% against a serotype II *Staphylococcus epidermidis*, such that the identified immunoglobulin is broadly reactive against *Staphylococcus epidermidis* serotypes I, II, and III, exhibits a high degree of binding to a TCA extract of serotype II *Staphylococcus epidermidis* by a high Optical Density of greater than 1 in an ELISA, has opsonophagocytic bactericidal activity of greater than or equal to 90% against a serotype II *Staphylococcus epidermidis*, and is for preventing bacteremia caused by a pathogenic coagulase-negative *Staphylococcus* infection.

12. Broadly reactive opsonophagocytic bactericidal immunoglobulin for preventing bacteremia caused by a pathogenic coagulase-negative *Staphylococcus* infection, obtained by the process comprising:
   a) obtaining an immunoglobulin source chosen from at least one of serum, plasma, immunoglobulin pool, whole blood, and tissue or cells that produce or contain antibodies;
   b) screening the immunoglobulin source to identify immunoglobulin that exhibits a high degree of binding to a TCA extract of serotype II *Staphylococcus epidermidis* by a high Optical Density of greater than 1 in an ELISA; and
   c) screening the immunoglobulin source of step b) to further identify immunoglobulin which has an opsonophagocytic bactericidal activity of greater than or equal to 90% against a serotype II *Staphylococcus epidermidis*, such that the identified immunoglobulin is broadly reactive against *Staphylococcus epidermidis* serotypes I, II, and III, exhibits a high degree of binding to a TCA extract of serotype II *Staphylococcus epidermidis* by a high Optical Density of greater than 1 in an ELISA, has opsonophagocytic bactericidal activity of greater than or equal to 90% against a serotype II *Staphylococcus epidermidis*, and is for preventing bacteremia caused by a pathogenic coagulase-negative *Staphylococcus* infection.

* * * * *